US011826364B2

(12) United States Patent
Copmans et al.

(10) Patent No.: US 11,826,364 B2
(45) Date of Patent: Nov. 28, 2023

(54) TREATMENT FOR EPILEPSY

(71) Applicants: Katholieke Universiteit Leuven, Leuven (BE); Technical University of Denmark, Kongens Lyngby (DK)

(72) Inventors: Daniëlle Copmans, Holsbeek (BE); Alexander Crawford, Oslo (NO); Peter De Witte, Kessel-Lo (BE); Camila Esguerra, Oslo (NO); Sara Kildgaard, Lyngby (DK); Thomas Ostenfeld Larsen, Holte (DK); Annelii Ny, Mol (BE)

(73) Assignees: Katholieke Universiteit Leuven, Leuven (BE); Technical University of Denmark, Kongens Lyngby (DK)

( * ) Notice: Subject to any disclaimer, the term of this patent is extended or adjusted under 35 U.S.C. 154(b) by 0 days.

(21) Appl. No.: 17/681,521

(22) Filed: Feb. 25, 2022

(65) Prior Publication Data
US 2022/0265638 A1    Aug. 25, 2022

Related U.S. Application Data

(63) Continuation of application No. 16/642,494, filed as application No. PCT/EP2018/073149 on Aug. 28, 2018, now abandoned.

(30) Foreign Application Priority Data

Aug. 28, 2017 (GB) ...................................... 1713762

(51) Int. Cl.
| | | |
|---|---|---|
| *A61K 31/4741* | (2006.01) | |
| *A61P 25/08* | (2006.01) | |
| *A61K 31/353* | (2006.01) | |
| *A61K 31/496* | (2006.01) | |

(52) U.S. Cl.
CPC ........ *A61K 31/4741* (2013.01); *A61K 31/353* (2013.01); *A61K 31/496* (2013.01); *A61P 25/08* (2018.01)

(58) Field of Classification Search
CPC ................................................. A61K 31/4741
See application file for complete search history.

(56) References Cited

U.S. PATENT DOCUMENTS

| | | | |
|---|---|---|---|
| 6,069,146 A | 5/2000 | Fenical | |
| 2017/0231923 A1 | 8/2017 | Guy et al. | |

OTHER PUBLICATIONS

Copmans, Mar. Drugs 2019, 17, 607.*
D. Crawford, et al., "Fishing for Drugs from Nature: Zebrafish as a Technology Platform for Natural Product Discovery", Planta Med; vol. 74; 2008; pp. 624-632.*

T. Afrikanova, et al., "Validation of the Zebrafish Pentylenetetrazol Seizure Model: Locomotor versus Electrographic Responses to Antiepileptic Drugs", PLOS ONE, www.plosone.org; vol. 8, Issue 1; Jan. 2013; 9 pgs.
S. C. Baraban, et al., "Pentylenetetrazole Induced Changes in Zebrafish Behavior, Neural Activity and C-Fos Expression", Neuroscience, vol. 131; 2005; pp. 759-768.
M. E. Barton, et al., "Pharmacological Characterization of the 6 Hz Psychomotor Seizure Model of Partial Epilepsy", Epilepsy Research, www.elsevier.com/locate/epilepsyres; vol. 47; 2001; pp. 217-227.
S. Berghmans, et al., "Zebrafish Offer the Potential for a Primary Screen to Identify a Wide Variety of Potential Anticonvulsants", Epilepsy Research, www.elsevier.com/locate/epilepsyres; vol. 75; 2007; pp. 18-28.
A. T. Berg, et al., "Revised Terminology and Concepts for Organization of Seizures and Epilepsies: Report of the ILAE Commission on Classification and Terminology, 2005-2009", Epilepsia; vol. 51; No. 4; 2010; pp. 676-685.
B. N. Blond, et al., "Assessment of Treatment Side Effects and Quality of Life in People with Epilepsy", Neurol Clin; vol. 34; 2016; pp. 395-410.
O. E. Buenafe, et al., "Tanshinone IIA Exhibits Anticonvulsant Activity in Zebrafish and Mouse Seizure Models", ACS Chemical Neuroscience, pubs.acs.org/chemoneuro; vol. 4; 2013; pp. 1479-1487.
N. Bunbamrung, et al., "Penicisochromans from the Endophytic Fungus *Penicillium* sp. BCC18034", Phytochemistry Letters, www.elsevier.com/locate/phytol; vol. 10; 2014; pp. 13-18.
D. Copmans, et al., "Methylated Flavonoids as Anti-Seizure Agents: Naringenin 4',7-Dimethyl Ether Attenuates Epileptic Seizures in Zebrafish and Mouse Models", Neurochemistry International, www.elsevier.com/locate/nci; vol. 112; 2018; pp. 124-133.
D. Copmans, et al., "A KNIME-Based Analysis of the Zebrafish Photomotor Response Clusters the Phenotypes of 14 Classes of Neuroactive Molecules", Journal of Biomolecular Screening; vol. 12, No. 5; 2016; pp. 427-436.
D. Copmans, et al., "Zebrafish-Based Discovery of Antiseizure Compounds from the Red Sea: Pseurotin $A_2$ and Azaspirofuran A", ACS Chemical Neuroscience, pubs.acs.org/chemneuro; vol. 9; 2018; pp. 1652-1662.
J. A. Cramer, et al., "Adverse Effects of Antiepileptic Drugs: a Brief Overview of Important Issues", Expert Ref. Neurother.; vol. 10; No. 6; 2010; pp. 885-891.
A. D. Crawford, et al., "Fishing for Drugs from Nature: Zebrafish as a Technology Platform for Natural Product Discovery", Planta Med; vol. 74; 2008; pp. 624-632.
L. Dalic, et al., "Managing Drug-Resistant Epilepsy: Challenges and Solutions", Neuropsychiatric Disease and Treatement; vol. 12; 2016; pp. 2605-2616.
R. S. Fisher, et al., Epileptic Seizures and Epilepsy: Definitions Proposed by the International League Against Epilepsy (ILAE) and the International Bureau for Epilepsy (IBE); Epilepsia; vol. 46, No. 4; 2005; pp. 470-472.

(Continued)

*Primary Examiner* — Nizal S Chandrakumar
(74) *Attorney, Agent, or Firm* — Blank Rome LLP

(57) ABSTRACT

The present invention discloses isoquinolines and 1H-2-Benzopyranes and their use in the treatment and prevention in epilepsy and other seizures. The present invention further discloses methods to screen isoquinoline- and 1H-2-Benzopyran-like molecules as pharmaceutically active compounds.

4 Claims, 9 Drawing Sheets

(56) References Cited

OTHER PUBLICATIONS

R. S. Fisher, et al., "Instruction Manual for the ILAE 2017 Operational Classification of Seizure Types", Epilepsia; vol. 58, No. 4; 2017; pp. 531-542.

A. Golyala, et al., "Drug Development for Refractory Epilepsy: The Past 25 Years and Beyond", Seizure, www.elsevier.com/locate/yseiz; vol. 44; 2017; pp. 147-156.

B. D. Klein, et al., "Evaluation of Cannabidiol in Animal Seizure Models by the Epilepsy Therapy Screening Program (ETSP)", Neurochem Res; vol. 42; 2017; pp. 1939-1948.

J. Kohno, et al., "Structures of TMC-120A, B and C, Novel Isoquinoline Alkaloids from *Aspergillus ustus* TC 1118", Tetrahedron; vol. 55; 1999; pp. 11247-11252.

K. Kuramochi, et al., "Synthesis, Structure, and Cytotoxicity Studies of Some Fungal Isochromanes", Journal of Natural Products, pubs.acs.org/jnp; vol. 76; 2013; pp. 1737-1745.

K. Kuramochi, et al., "Synthesis and Structural Characterization of Natural Benzofuranoids", Journal of Natural Products, pubs.acs.org/jnp; vol. 78; 2015; pp. 1056-1066.

I. E. Scheffer, et al., "ILAE Classification of the Epilepsies Position Paper of the ILAE Commission for Classification and Terminology", Epilepsia; vol. 58, No. 4; Apr. 2017; pp. 512-521.

Z. Lu et al., "Sesquiterpenoids and Benzofuranoids from the Marine-Derived Fungus *Aspergillus ustus* 094102", J. Nat. Prod.; vol. 72; 2009; pp. 1761-1767.

C. A. MacRae, et al., "Zebrafish as Tools for Drug Discovery", Nature Reviews; vol. 14; Oct. 2015; pp. 721-731.

S. I. Moshe, et al., "Epilepsy: New Advances", Seminar, www.thelancet.com; vol. 385; Mar. 7, 2015; pp. 884-898.

A. K. Ngugi, et al., "Estimation of the Burden of Active and Life-Time Epilepsy: A Meta-Analytic Approach", Epilepsia; vol. 51; No. 5; 2010; pp. 883-890.

A. M. Orellana-Paucar, et al., "Insights from Zebrafish and Mouse Models on the Activity and Saftey of Ar-Turmerone as a Potential Drug Candidate for the Treatment of Epilepsy", PLOS One, www.plosone.org; vol. 8; Issue 12; Dec. 2013; 14 pgs.

A. M. Orellana-Paucar, et al., "Anticonvulsant Activity of Bisabolene Sesquiterpenoids of *Curcuma longa* in Zebrafish and Mouse Seizure Models", Epilepsy & Behavior, www.elsevier.com/locate/yebeh; vol. 24; 2012; pp. 14-22.

R. M. Patel, et al., "Cytotxic Activity of Methanolic Extract of *Artocarpus heterophyllus* against A549, Hela MCF-7 Cell Lines", Journal of Applied Pharmaceutical Science 01; vol. 7; 2011; pp. 167-171.

J. Perez, et al., "A Novel in Vitro Approach for Simultaneous Evaluation of CYP3A4 Inhibition and Kinetic Aqueous Solubility", Journal of Biomolecular Screening; vol. 20, No. 2; 2015; pp. 254-264.

J. W. Sander, "The Epidemilogy of Epilepsy Revisited", Curr Opin Neurol; vol. 16; 2003; pp. 165-170.

A. Singh, MD, et al., "The Epidemiology of Global Epilepsy", Neurol Clin; vol. 34; 2016; pp. 837-847.

G. J. Slack, et al., "Secondary Metabolites from *Eurotium* Species, *Aspergillus calidoustus* and *A. insuetus* Common in Canadian Homes with a Review of their Chemistry and Biological Activities", Mycological Research, www.elsevier.com/locate/mycres; vol. 113; 2009; pp. 480-4903

K. S. Wilcox, et al., "Issues Related to Development of New Anti-Seizure Treatments", Epilepsia, vol. 54, Nos. 0 4; Aug. 2013; pp. 24-34.

International Search Report and Written Opinion for PCT/EP2018/073149, dated Dec. 5, 2018, 9 pages.

S. O. Simonetti, et al., "Angular Tricyclic Benzofurans and Related Natural Products of Fungal Origin. Isolation, Biological Activity and Synthesis", Natural Product Reports, 2013, 1 page.

"Structures of TMC-120A, B and C, Novel Isoquinoline Alkaloids from Aspergillus Ustus TC 1118", https://doi.org/10.1016/S0040-4020(99)00648-1, Tetrahedron, vol. 55, Issue 37, Sep. 1999, pp. 11247-11252.

Kohno, Tetrahedron (1999), 55(37), 11247-11252.

Mishra, Biomedicine & Pharmacotherapy (2008), 62(2), 94-98.

Yamazaki, Advances in Experimental Medicine and Biology (2009), 611 (Peptides for Youth), 524-528).

Kohno, Journal of Antibiotics, Vo. 52, No. 10, Oct. 1999.

Bunbamrung, Phytochemistry Letters, (2014), 10, 13-18.

* cited by examiner

TMC-120A

TMC-120B

TMC-120C

Penicisochroman G

Ustusorane B

Compound 6

Compound 7

TREATMENT FOR EPILEPSY

This patent application is a continuation application of U.S. patent application Ser. No. 16/642,494, filed on Feb. 27, 2020, which is the U.S. national phase application of International Application No. PCT/EP2018/073149, filed on Aug. 28, 2018, which claims priority to Great Britain Patent Application No. 1713762.1, filed on Aug. 28, 2017. The contents of each of these applications are incorporated herein by reference in their entireties.

FIELD OF THE INVENTION

The present invention provides a pharmaceutical composition for treating epilepsy.

BACKGROUND OF THE INVENTION

Epilepsy is among the most common severe neurological conditions, affecting more than 70 million people worldwide [Sander (2003) Curr Opin Neurol 16, 165-170; Ngugi et al. (2010) Epilepsia 51, 883-890; Singh and Trevick (2016) Neurol Clin 34, 837-847]. It is characterized by an enduring predisposition of the brain to generate epileptic seizures, with neurobiologic, cognitive, psychological, and social consequences [Fisher et al. (2005) Epilepsia 46, 470-472.]. The treatment of epilepsy consists mostly of pharmacotherapy with antiseizure drugs (ASDs) to control seizures [Golyala & Kwan (2017) Seizure 44, 147-156.]. Despite considerable efforts, current ASDs fail to control the seizures of 30% of patients due to drug-resistance [Dalic & Cook (2016) Neuropsychiatr Dis Treat 12, 2605-2616.]. Uncontrolled epilepsy can result in a poorer quality of life because of physical, psychological, cognitive, social, and occupational problems [Golyala, A., and Kwan, P. (2017) Seizure 44, 147-156; Blond et al. (2016) Neurol Clin 34, 395-410, viii]. Moreover, first-line ASDs are associated with important adverse effects that can significantly impact daily life and are a main cause of treatment failure [Dalic & Cook (2016) Neuropsychiatr Dis Treat 12, 2605-2616; Moshe et al. (2015) Lancet 385, 884-898; Cramer et al (2010) Expert Rev Neurother 10, 885-891].

Hence, there is a high need for the development of safer ASDs that are more effective against drug-resistant seizures.

Zebrafish animal models for screening compounds for anti-epileptic activity has been described [e.g. MacRae & Peterson (2015) Nat Rev Drug Discov 14, 721-731; Crawford et al. (2008) Planta Med 74, 624-632]

SUMMARY OF THE INVENTION

The present invention discloses isoquinoline alkaloids which were isolated from the bioactive marine-derived fungus *Aspergillus insuetus*. The compounds were investigated for antiseizure activity in the larval zebrafish PTZ seizure model. TMC-120A and TMC-120B were found to have antiseizure activity. The antiseizure activity of TMC-120A and TMC-120B translated to a mouse model of drug-resistant focal seizures. Following structural analogues of TMC-120A and TMC-120B are candidate compounds for antiseizure activity in the larval zebrafish PTZ seizure model: TMC-120C, penicisochroman G, ustusorane B, 7-methylfuro[3,2,h]isoquinoline-3(2H)-one, 7-methylfuro[3,2-h]isoquinoline-3(2H)-one (compound 6), 2-(7-methyl-2,3-dihydrofuro[3,2-h]isoquinoline-2-yl)-propan-2-ol (compound 7).

Based on the prominent antiseizure activity in zebrafish, the present invention relates to TMC-120A, TMC-120B, TMC-120C, penicisochroman G, ustusorane B, 7-methylfuro[3,2,h]isoquinoline-3(2H)-one, compound 6, and compound 7 as compounds in the use for the treatment of drug-resistant focal seizures, and in the treatment of epilepsy in general.

The present invention demonstrates antiseizure activity of certain isoquinoline alkaloids, and gives another example of the translation of results from zebrafish larvae to mice.

The present invention accordingly relates to the screening of other isoquinoline alkaloids and modified versions thereof for compounds which are suitable for the prevention and treatment of seizures.

The invention relates to compounds for use in the treatment or prevention of seizures and/or epilepsy.

The invention relates to compounds for use in the treatment or prevention of epilepsy, epileptic seizures and other seizures, and in the treatment or prevention of the symptoms of epilepsy.

The invention is summarized in the following statements:

A compound comprising a moiety selected from the gr formula oup consisting of the moieties with formula 1, formula 2, formula 3, formula 4, formula 5 and formula 6.

1. An isoquinoline or 1H-2-Benzopyran, selected from the group consisting of TMC-120A, TMC-120B, TMC-120C, penicisochroman G, ustusorane B, compound 6 and compound 7, for use in the treatment or prevention of epilepsy.

2. An isoquinoline or 1H-2-Benzopyran in accordance with statement 1, in combination with halimide or plinabulin, for use in the treatment or prevention of epilepsy.

3. A method for identifying pharmaceutical compounds against epilepsy, the method comprising the steps of:

providing a compound which comprises a moiety of a benzene ring attached to a pyridine ring or puran ring and further comprising a modified or unmodified furan group attached to the benzene ring, and, as depicted in formula 1 or formula 2

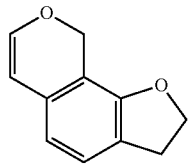
(Formula 1)

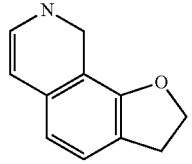
(Formula 2)

testing the compound for antiseizure activity.

4. The method according to statement 3, wherein said pyridine or puran ring is further methylated as depicted as depicted in Formula 3 or Formula 4

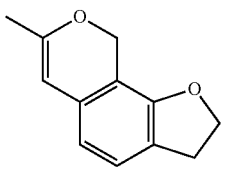

Formula (3)

(formula 4)

5. The method according to statement 3 or 4, wherein the compound comprises the moiety as depicted in Formula 5 or Formula 6.

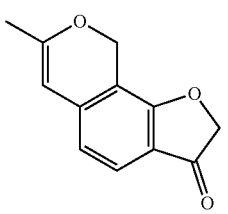

(Formula 5)

(formula 6)

Thus the methods of the present invention envisage the testing of a compound which comprises a moiety as depicted in formula 1, 2, 3, 4, 5, or 6.

6. The method according to statement 3, 4 or 5, which comprises an isoquinoline or 1H-2-Benzopyran moiety and testing the compound for antiseizure activity.
7. The method according to any one of statement 3 to 6, wherein the compound with a isoquinoline or 1H-2-Benzopyran moiety is a TMC-120A, TMC-120B, TMC-120C, penicisochroman G, ustusorane B, compound 6 and compound 7.
8. The method according to any one of statements 3 to 7, wherein halimide or plinabulin added to said compound for testing antiseizure activity.
9. The method according to any one of statements 3 to 8, wherein the isoquinoline or 1H-2-Benzypuran is a compound as depicted in FIG. 1 and/or 2, with modified molecular structure or stereochemistry.
10. The method according to any one of statements 3 to 9, wherein anti-seizure activity is determined in a zebrafish model.
11. The method according to any one of statements 3 to 10, wherein anti-seizure activity is further determined in a mammalian model.
12. The method according to any one of statements 3 to 11, further comprising the step of testing the compound for a side effect.
13. The method according to any one of statements 3 to 12, further comprising the step of formulating a compound with determined anti-seizure activity into a pharmaceutical composition with an acceptable carrier, for use in the treatment of epilepsy.

DETAILED DESCRIPTION OF THE INVENTION

ABBREVIATIONS USED IN THE APPLICATION

Figure 1:
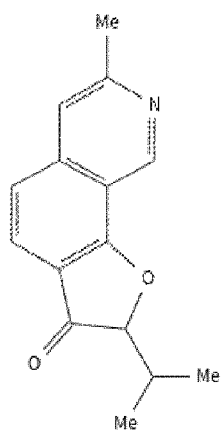
FIG. 1. TMC-120A and TMC-120B, chemical structures isolated from extracts of the fungus Aspergillus insuetus.
Figure 1:
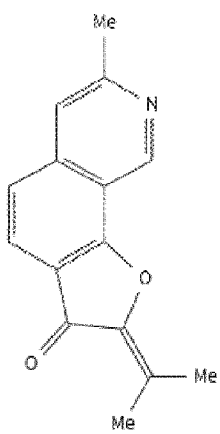

ASD, antiseizure drug; CV, column volume; CYA, Czapek Yeast extract agar; dpf, days post-fertilization; DAD, diode array detection; DCM, dichloromethane; DMSO, dimethyl sulfoxide; EtOAc, ethyl acetate; FA, formic acid; FP7, Seventh Framework Programme; LFP, local field potential; MeCN, acetonitrile; MeOH, methanol; min, minute; MTC, maximum tolerated concentration; NP, natural product; PEG200, polyethylene glycol M.W. 200; PMR, photomotor response; PTZ, pentylenetetrazole; $t_{1/2}$, half-life; UHPLC-DAD-QTOFMS, Ultra-high performance liquid chromatography-diode array detection-quadrupole time of flight mass spectrometry; VHC, vehicle; YES, Yeast extract sucrose agar Definitions "Isoquinoline" is a heterocyclic organic compound. It is a structural isomer of quinolone. Isoquinoline and quinolone are benzopyridines, which are composed of a benzene ring fused to a pyridine ring. The compounds of the present invention are isoquinolines which are substituted with molecular structures with an unmodified or modified furan group such as dihydrofuran-3-one. Other compounds of the present invention consist of a benzene ring fused to a puran ring (1H-2-Benzopyran). The 1H-2-Benzopyran is substituted with molecular structures such as dihydrofuran-3-one with an unmodified or modified furan group. The above indicated medical use of the compounds equally comprises the use of the salt form thereof. Pharmaceutically acceptable salts include those described by Berge, Bighley and Monkhouse, J. Pharm. Sci., 1977, 66, 1-19. Compounds are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The corresponding stereospecific name and structure have been assigned to the final product where the enantiomeric excess of said product is greater than 70%. Assignment of absolute stereochemistry is based on the known chirality of the starting material. In examples where the composition of the final product has not been characterised by chiral HPLC, the stereochemistry of the final product has not been indicated. However, the chirality of the main component of the product mixture will be expected to reflect that of the starting material and the enantiomeric excess will depend on the synthetic method used and is likely to be similar to that measured for an analogous example (where such an example exists). Thus compounds shown in one chiral form are expected to be able to be prepared in the alternative chiral form using the appropriate starting material. Alternatively, if racemic starting materials are used, it would be expected that a racemic product would be produced and the single enantiomers could be separated by the usual methods. The invention also extends to any tautomeric forms and mixtures thereof. "Seizure" refers to a brief episode of signs or symptoms due to abnormal excessive or synchronous neuronal activity in the brain. The outward effect can vary from uncontrolled jerking movement (tonic-clonic seizure) to as subtle as a momentary loss of awareness (absence seizure). Seizure types are typically classified on observation (clinical and EEG) rather than the underlying pathophysiology or anatomy.

I Focal seizures (Older term: partial seizures)
  IA Simple partial seizures—consciousness is not impaired
    IA1 With motor signs
    IA2 With sensory symptoms
    IA3 With autonomic symptoms or signs
    IA4 With psychic symptoms IB Complex partial seizures—consciousness is impaired (Older terms: temporal lobe or psychomotor seizures)
  IB1 Simple partial onset, followed by impairment of consciousness
  IB2 With impairment of consciousness at onset
IC Partial seizures evolving to secondarily generalized seizures
  IC1 Simple partial seizures evolving to generalized seizures
  IC2 Complex partial seizures evolving to generalized seizures
  IC3 Simple partial seizures evolving to complex partial seizures evolving to generalized seizures
II Generalized seizures
IIA Absence seizures (Older term: petit mal)
  IIA1 Typical absence seizures
  IIA2 Atypical absence seizures
IIB Myoclonic seizures
IIC Clonic seizures
IID Tonic seizures,
IIE Tonic-clonic seizures (Older term: grand mal)
IIF Atonic seizures
III Unclassified epileptic seizures "Epilepsy" is a condition of the brain marked by a susceptibility to recurrent seizures. There are numerous causes of epilepsy including, but not limited to birth trauma, perinatal infection, anoxia, infectious diseases, ingestion of toxins, tumors of the brain, inherited disorders or degenerative disease, head injury or trauma, metabolic disorders, cerebrovascular accident and alcohol withdrawal. A large number of subtypes of epilepsy have been characterized and categorized. The classification and categorization system, widely accepted in the art, is that adopted by the International League Against Epilepsy's ("ILAE") Commission on Classification and Terminology [See e.g., Berg et al. (2010) *Epilepsia* 51, 676-685:

I. Electrochemical syndromes (arranged by age of onset):
  I.A. Neonatal period: Benign familial neonatal epilepsy (BFNE), Early myoclonic encephalopathy (EME); Ohtahara syndrome
  I.B. Infancy: Epilepsy of infancy with migrating focal seizures; West syndrome; Myoclonic epilepsy in infancy (MEI); Benign infantile epilepsy; Benign familial infantile epilepsy; Dravet syndrome; Myoclonic encephalopathy in non-progressive disorders
  I.C. Childhood: Febrile seizures plus (FS+) (can start in infancy); Panayiotopoulos syndrome; Epilepsy with myoclonic atonic (previously astatic) seizures; Benign epilepsy with centrotemporal spikes (BECTS); Autosomal-dominant nocturnal frontal lobe epilepsy (ADNFLE); Late onset childhood occipital epilepsy (Gastaut type); Epilepsy with myoclonic absences; Lennox-Gastaut syndrome; Epileptic encephalopathy with continuous spike-and-wave during sleep (CSWS), also known as Electrical Status Epilepticus during Slow Sleep (ESES); Landau-Kleffner syndrome (LKS); Childhood absence epilepsy (CAE)
  I.D. Adolescence-Adult: Juvenile absence epilepsy (JAE); Juvenile myoclonic epilepsy (JME); Epilepsy with generalized tonic-clonic seizures alone; Progressive myoclonus epilepsies (PME); Autosomal dominant epilepsy with auditory features (ADEAF); Other familial temporal lobe epilepsies
  I.E. Less specific age relationship: Familial focal epilepsy with variable foci (childhood to adult); Reflex epilepsies II. Distinctive constellations
  II.A. Mesial temporal lobe epilepsy with hippocampal sclerosis (MTLE with
  II.B. Rasmussen syndrome
  II.C. Gelastic seizures with hypothalamic hamartoma
  II.D. Hemiconvulsion-hemiplegia-epilepsy
  II.E. Epilepsies that do not fit into any of these diagnostic categories, Distinguished on the basis of Presumed cause (presence or absence of a known structural or metabolic condition) or on the basis of Primary mode of seizure onset (generalized vs. Focal)
III. Epilepsies attributed to and organized by structural-metabolic causes
  III.A. Malformations of cortical development (hemimegalencephaly, heterotopias, etc.)
  III.B. Neurocutaneous syndromes (tuberous sclerosis complex, Sturge-Weber, etc.)
  III.C. Tumor
  III.D. Infection
  III.E. Trauma
  IV. Angioma
  IV.A. Perinatal insults
  IV.B. Stroke
  IV.C. Other causes
V. Epilepsies of unknown cause
VI. Conditions with epileptic seizures not traditionally diagnosed as forms of epilepsy per se
  VI.A. Benign neonatal seizures (BNS)
  VI.B. Febrile seizures (FS)

A newer classification is found in Scheffer et al. (2017) *Epilepsia* 58, 512-521.

A first aspect of the present invention relates to an isoquinoline compound or a 1H-2-benzopyran compound for use in the treatment or prevention of epilepsy, more particularly for preventing a alleviating seizures.

Figure 2:
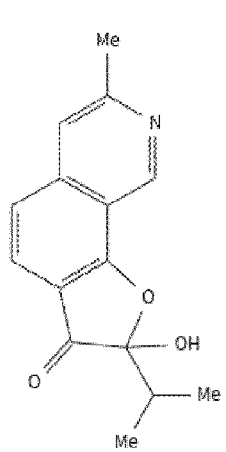
FIG. 2. Chemical structures identified based on structural analogy with TMC-120A and TMC-120B. compound 6 stands for 7-methylfuro[3,2-h]isoquinoline-3(2H)-one; compound 7 stands for 2-(7-methyl-2,3-dihydrofuro[3,2-t]isoquinoline-2-yl)-propan-2-ol.
Figure 2:
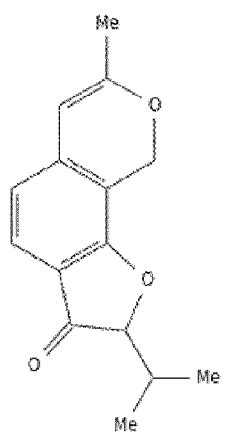
Figure 2:
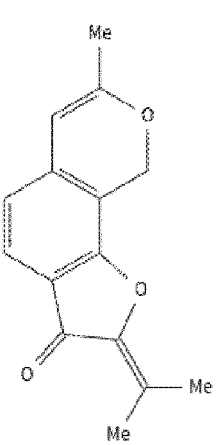
Figure 2:
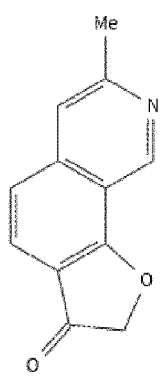
Figure 2:
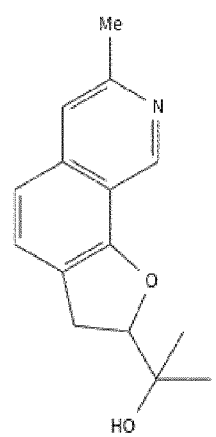

Preferred compounds are TMC-120A, TMC-120B, TMC-120C, penicisochroman G and ustusorane B (depicted in FIG. 1 or 2).

The examples of the present invention used specific compounds isolated from two *Aspergillus* strains. Herein some are effective in the zebrafish and mouse seizure models, while other show no pharmaceutical activity. The screening did not include all isoquinoline compounds or all 1H-2-Benzopyran compounds described in the literature, let alone chemically modified versions.

The present invention relates in another aspect to methods to identify other isoquinoline or 1H-2-Benzopyran models in the zebrafish and mouse model to identify compounds with a similar or higher activity than TMC-120A, TMC-120B, TMC-120C, penicisochroman G, ustusorane B, and or with better ADMET properties.

Another aspect of the present invention relates to methods for identifying compounds which are active in models for determining anti-seizure activity. Envisaged compounds are structurally related to the compounds depicted in FIG. 1. The envisaged compounds all comprise a moiety of a benzene ring fused to a pyridine ring or a moiety of a benzene ring fused to a puran ring. The envisaged compounds typically further comprise a modified or unmodified furan group attached to the benzene ring.

Thus the compounds comprise a benzene ring fused to a) a pyridine ring or a puran ring and b) fused to a modified or unmodified furan group, The envisaged compounds are typically further methylated on the pyridine or puran group, generally on the position as shown in FIG. 1.

Examples of suitable compounds are e.g. disclosed in Kuramochi and Tsubaki (2015) *Nat. Prod.* 78, 1056-1066, Kuramochi et al. (2013) *J Nat Prod.* 76, 1737-1745, Bumbamrung et al. (2014) *Phytochem Lett.* 10, 13-18, and Slack et al (2009) *Mycol. Res.* 113, 480-490

Methods of the present invention for drug screening can be advantageously performed with a zebrafish model which is suitable for large-scale screening and captures the complexity of a whole body organism and the central nervous system. As a vertebrate, zebrafish are highly similar to humans due to a high genetic, physiological and pharmacological conservation. Moreover, given the small size of embryos and larvae, they fit in the well of microtiter plates and hence are suitable for medium to high-throughput testing [Howe et al, MacRae and Peterson, Khan et al. cited above]. Given the low volumes used in 96- and 384-well plates, zebrafish larvae only require small amounts of sample in the low microgram range when added to their swimming water and even less when administered by injection. This property is of particular interest for marine natural product drug discovery, where material is often scarce [West and Crawford, cited above]. A particular suitable larval zebrafish seizure and epilepsy model, is the larval zebrafish pentylenetetrazole (PTZ) seizure model. This model has the following advantages 1) the model has been extensively characterized in terms of behavioral and non-behavioral seizure markers, 2) it has been pharmacologically characterized with ASDs on the market, 3) results translate well to rodent models, 4) seizures can easily and rapidly be induced by a single administration of the convulsant drug to the larva's aqueous environment, and 5) seizures can be quantified automatically by video recording [Baraban et al. (2005) *Neuroscience* 131, 759-768; Afrikanova et al. (2013) *PLoS One* 8, e54166; Berghman et al. (2007) *Epilepsy Res* 75, 18-28; Buenafe et al. (2013) *ACS Chem Neurosci* 4, 1479-1487; Patel and Patel (2011) *J. App. Pharm. Sci.* 1, 167-171].

Within the framework of PharmaSea, two isoquinoline alkaloids TMC-120A and TMC-120B were isolated from the bioactive marine-derived fungus Aspergillus insuetus, which was isolated from a seawater trap set in the North Sea, in between Norway and Denmark. Both compounds were investigated for antiseizure activity in the larval zebrafish PTZ seizure model, after acute and chronic exposure. In addition, electrophysiological analysis from the zebrafish midbrain demonstrated that TMC-120A and TMC-120B also significantly lowered PTZ-induced epileptiform discharges. In addition, other isoquinoline compounds were identified based on structural homology to TMC-120A and TMC-120B. These compounds are TMC-120C, penicisochroman G, ustusorane B, compound 6 and compound 7. All compounds demonstrated to have antiseizure activity in the larval zebrafish PTZ seizure model, after acute exposure.

Methods of the present invention for drug screening can be equally performed in a mammalian model, wherein generally those compounds are tested which already gave positive results in the above mentioned zebrafish model.

Accordingly, TMC-120A and TMC-120B were tested in the mouse 6-Hz (44 mA) psychomotor seizure model.

Herein, treatment with TMC-120A and TMC-120B shortened the seizure duration, thereby confirming the antiseizure activity observed in the zebrafish model. These results not only confirmed the translation of results from zebrafish larvae to mice but also indicates that TMC-120A and TMC-120B are effective against drug-resistant focal seizures.

Methods of the present invention for drug screening can further comprise the step of determining parameters such as absorption, distribution, metabolism, and excretion—toxicity.

In summary, based on the prominent antiseizure activity seen in a standard zebrafish and mouse seizure model and their ADMET characteristics, the present invention claims TMC-120A, TMC-120B, TMC-120C, penicisochroman G, ustusorane B, compound 6 and compound 7 as compounds for use in the treatment of seizures and/or epilepsy.

EXAMPLES

Example 1

Methods 1.1. Chemical Experimental Procedures

Ultra-high performance liquid chromatography-diode array detection-quadrupole time of flight mass spectrometry (UHPLC-DAD-QTOFMS) was performed on an Agilent Infinity 1290 UHPLC system (Agilent Technologies, Santa Clara, Calif., USA) equipped with a diode array detector (DAD). Separation was achieved on an Agilent Poroshell 120 phenyl-hexyl column (2.1×150 mm, 2.7 μm) with a flow of 0.35 mL/min at 60° C. using a linear gradient 10% acetonitrile (MeCN) in Milli-Q water buffered with 20 mM formic acid (FA) increased to 100% in 15 min staying there for 2 min, returned to 10% in 0.1 min and kept there for 3 min before the following run. MeCN was LC-MS grade. MS detection was done on an Agilent 6550 iFunnel QTOF MS equipped with Agilent Dual Jet Stream electrospray ion source with the drying gas temperature of 160° C. and gas flow of 13 L/min and sheath gas temperature of 300° C. and flow of 16 L/min. Capillary voltage was set to 4000 V and nozzle voltage to 500 V. Data processing was performed using Agilent MassHunter Qualitative Analysis for quadrupole time of flight (version B.07.00). Pre-fractionation was performed using flash chromatography of the crude extract with an Isolera one automated flash system (Biotage, Uppsala, Sweden). Purification of compounds was conducted using a Waters 600 Controller (Milford, Mass., USA) coupled to a Waters 996 Photodiode Array Detector. One and two dimensional (1D and 2D) NMR experiments were acquired using standard pulse sequences on either a 600 MHz Bruker Ascend spectrometer with a SmartProbe (BBO), a 400 MHz Bruker Ascend spectrometer with a Prodigy cryoprobe or a 800 MHz Bruker Avance spectrometer with a 5 mm TCI cryoprobe. Optical rotations were measured on a Perkin Elmer 341 polarimeter (Perkin Elmer, Waltham, Mass., USA).

1.2. Microbial Strain and Microbial Cultivation

*Aspergillus insuetus* IBT 28443 and IBT 28485 were from the IBT culture collection at the Department of Biotechnology and Biomedicine, Technical University of Denmark. The fungus *Aspergillus insuetus* IBT 28443 was collected at the Galathea 3 expedition and isolated from a seawater trap set in the North Sea, in between Denmark and Norway.

*Aspergillus insuetus* IBT 28443 was cultivated on one CYA and one YES media plates for 9 days in the dark at 25° C. for the original combined small scale extract. For the individual small scale extracts the fungus was cultivated on eight plates of CYA, eight plates of YES and eight plates of OAT for 9 days in the dark at 25° C. For the large scale extract the fungus was cultivated on 250 plates of CYA for 9 days in the dark at 25° C.

*Aspergillus insuetus* IBT 28485 was cultivated on 220 CYA plates for 7 days in the dark at 25° C.

1.3. Microbial Extraction Aand Isolation

For the original combined small scale extract of *Aspergillus insuetus* IBT 28443 the two plates in total (one CYA and one YES) were extracted with 40 mL ethyl acetate (EtOAc) containing 1% FA. The crude extract was then fractionated on a reversed phase C18 flash column (Sepra ZT, Isolute, 10 g) using an Isolera One automated flash system (Biotage, Uppsala, Sweden). The gradient used was 15%-100% MeCN buffered with 20 mM FA over 28 min (12 mL/min). Six flash fractions were automatically collected based on UV signal (210 nm and 254 nm). For the individual small scale extracts on CYA, YES and OAT each of the separate set of eight plates were extracted with 150 mL EtOAc with 1% FA and for the large scale extract on CYA it was extracted with 150 mL EtOAc with 1% FA for every 10 plates. All the crude extracts were fractionated on a reversed phase Cis flash column (Sepra ZT, Isolute, 25 g/33 mL) using the Isolera One automated flash system. The gradient was 10% stepwise (12 column volumes) from 15% to 100% MeCN buffered with 20 mM FA with a flow of 25 mL/min. Fractions were collected manually for every 10%. For the large scale extract the most bioactive fraction (25% MeCN) was fractionated on a reversed phase Isolute SPE column (500 mg/3 mL) using methanol (MeOH) buffered with 20 mM FA. The compounds were eluted with 2 column volumes (CV) per fraction: 15% MeOH, 20% MeOH, 30% MeOH, 40% MeOH, 50% MeOH, 60% MeOH, 80% MeOH and 100% MeOH. From the 60% MeOH and 80% MeOH isolera fractions TMC-120A and TMC-120B separation was achieved on a Gemini C6 Phenyl, 5 µm, 250×10 mm column (Phenomenex, Torrance, CA, USA) with a flow of 4 mL/min. A linear gradient was used of 40%

MeCN in Milli-Q water with 20 mM FA going to 70% MeCN in 30 min. For the large scale extract of Aspergillus insuetus IBT 28485, the 220 Petri dish plates were extracted with 150 mL EtOAc with 1% FA for every 10 plates. The crude extract was fractionated on a diol flash column (Diol, 25 g, 33 mL) using the Isolera One automated flash system. The compounds were eluted with 2 CV per fraction: heptane, heptane 1:1 dichloromethane (DCM), DCM, DCM 1:1 EtOAc, EtOAc, EtOAc 1:1 MeOH and MeOH. The DCM, DCM 1:1 EtOAc and EtOAc fractions were further fractionated on the Isolera One flash system on a reversed phase C18 flash column (15 µm/100 Å, 10 g/15 mL) using MeOH buffered with 20 mM FA with a flow of 15 mL/min. Compounds were eluted with 6 CV per fraction: 35% MeOH, 40% MeOH, 42% MeOH, 45% MeOH, 47% MeOH, 50% MeOH, 55% MeOH, 60% MeOH, 70% MeOH, 80% MeOH and 100% MeOH. From the 42% and 45% MeOH isolera fractions TMC-120A and TMC-120B separation was achieved on a Gemini C6 Phenyl, 5 µm, 250×10 mm column (Phenomenex, Torrance, Calif., USA) with a flow of 4 mL/min using a linear gradient 40% MeCN in Milli-Q water with 20 mM FA going to 70% MeCN in 30 min. TMC-120C (from fraction 40% MeOH) separation was achieved on a Gemini C6 Phenyl, 5 µm, 250×10 mm column (Phenomenex, Torrance, Calif., USA) with a flow of 4 mL/min and using a linear gradient of 30% MeCN in Milli-Q water going to 60% MeCN in 30 min. Penicisochroman G and ustusorane B (from fractions 70% MeOH and 80% MeOH) separation was achieved on a Gemini $C_6$ Phenyl, 5 µm, 250×10 mm column (Phenomenex, Torrance, Calif., USA) with a flow of 4 ml/min using a linear gradient 65% MeCN in Milli-Q water with 20 mM FA going to 85% MeCN in 30 min. TMC-120A: pale yellow solid; $[\alpha]_D^{20}$ −5 (c 0.51, MeOH); UV (MeCN) λmax: 214 nm, 245 nm, 344 nm, 360 nm; HRESIMS m/z 242.1177 [M+H]$^+$ (calculated for $C_{15}H_{16}NO_2$, m/z 242.1176, Δ−0.32)

TMC-120B: slightly pale yellow needles; UV (MeCN) λmax: 214 nm, 240 nm, 262 sh nm, 275 nm, 296 sh nm, 306 nm, 369 nm; HRESIMS m/z 240.1019 [M+H]$^+$ (calculated for $C_{15}H_{14}NO_2$, m/z 240.1019, Δ 0.14)

1.4. Compound and Sample Preparation

For experiments with zebrafish larvae, dry samples and compounds were dissolved in 100% dimethyl sulfoxide (DMSO, spectroscopy grade) as 100-fold concentrated stocks and diluted in embryo medium to a final concentration of 1% DMSO content, except for PTZ which was dissolved in embryo medium (0% DMSO). Control groups were treated with 1% DMSO (VHC) in accordance with the final solvent concentration of tested samples or compounds. For mice experiments, a mixture of poly-ethylene glycol M.W. 200 (PEG200) and 100% DMSO (spectroscopy grade) (1:1 PEG200:DMSO) was used as solvent and VHC. Pentylenetetrazole and valproate were purchased from Sigma-Aldrich.

1.5. Experimental Animals

All animal experiments carried out were approved by the Ethics Committee of the University of Leuven (approval numbers 101/2010, 061/2013, 150/2015, 023/2017, and 027/2017) and by the Belgian Federal Department of Public Health, Food Safety & Environment (approval number LA1210199).

Zebrafish

Adult zebrafish (Danio rerio) stocks of AB strain (Zebrafish International Resource Center, Oregon, USA) were maintained at 28.0° C., on a 14/10 hour light/dark cycle under standard aquaculture conditions. Fertilized eggs were collected via natural spawning and raised in embryo medium (1.5 mM HEPES, pH 7.2, 17.4 mM NaCl, 0.21 mM KCl, 0.12 mM MgSO4, 0.18 mM Ca(NO3)2, and 0.6 µM methylene blue) at 28.0° C., under constant light with regards to the zebrafish PTZ seizure model and under a 14/10 hour light/dark cycle with regards to the zebrafish photomotor response assay Mice Male NMRI mice (weight 18-20 g) were acquired from Charles River Laboratories and housed in poly-acrylic cages under a 14/10-hour light/dark cycle at 21° C. The animals were fed a pellet diet and water ad libitum, and were allowed to acclimate for one week before experimental procedures were conducted. Prior to the experiment, mice were isolated in a poly-acrylic cage with a pellet diet and water ad libitum for habituation overnight in the experimental room, to minimize stress.

1.6 Zebra Fish Photomotor Response Assay

Behavioral Analysis

Experiments were performed as described in Copmans et al. (2016) *J. Biomol Screen* 21, 427-436. In the primary screen one replicate well was used per sample tested and each experimental plate contained 6 internal control wells. Each well held 5 embryos that were incubated with sample for 2 hours prior to behavioral recording at 32 hpf. A neuroactive hit was defined as a marine NP that modified the PMR such that its behavioral fingerprint (16 pseudo Z-scores that together describe the embryonic motion over a 30 second recording period) contained at least one pseudo Z-score with an absolute value equal to or exceeding 5.

Toxicity Evaluation

Each behavioral analysis was followed by visual evaluation of the embryos under a light microscope to assess toxicity of treatment. Overall morphology, heartbeat, and touch response were investigated. Marine NPs were scored normal or toxic. When embryos showed normal morphology, normal or lowered heartbeat, and normal or lowered touch response the treatment was considered to be normal. In case of an abnormal morphology and/or absence of touch response or heartbeat a treatment was considered to be toxic.

1.7. Zebrafish Pentylenetetrazole Seizure Model

Toxicity Evaluation

Maximum tolerated concentration (MTC) was determined prior to further experiments and used as the highest test concentration. Experiments were described as described in Copmans et al. (2018) ACS chemical neuroscience. MTC was investigated by exposing 12 larvae of 6 dpf to a range of concentrations in a 100 μl volume during 18 hours. The following parameters were investigated after 2 and 18 hours of exposure: touch response, morphology, posture, edema, signs of necrosis, swim bladder, and heartbeat. MTC was defined as the highest concentration at which no larvae died nor showed signs of toxicity or locomotor impairment in comparison to VHC-treated control larvae.

For screening purposes, no MTC was determined, but behavioral analysis was followed by visual evaluation of the larvae under a light microscope to assess toxicity of treatment. Overall morphology, heartbeat, and touch response were investigated. Marine NPs were scored normal or toxic. When embryos showed normal morphology, heartbeat, and touch response the treatment was considered to be normal. In case of an abnormal morphology and/or absence of touch response or heartbeat a treatment was considered to be toxic.

Behavioral Analysis

Experiments were performed as [Add references please: Copmans (2018), ACS chemical neuroscience; Copmans et al. (2018) *Neurochem. Int.* 112, 124-133; Afrikanova et al. (2013) *PLoS One* 8, e54166; Orellana-Paucar et al. (2012) Epilepsy Behav 24, 14-22]. In brief, a single 7 dpf larva was placed in each well of a 96-well plate and treated with either VHC (1% DMSO) or test compound in a 100 μl volume. Larvae were incubated in dark for 2 hours at 28° C., whereafter 100 μl of either VHC (embryo medium) or 40 mM PTZ (20 mM working concentration) was added to each well. Next, within 5 minutes the 96-well plate was placed in an automated tracking device (ZebraBox Viewpoint, France) and larval behavior was video recorded for 30 minutes. The complete procedure was performed in dark conditions using infrared light. Total locomotor activity was recorded by ZebraLab software (Viewpoint, France) and expressed in actinteg units, which is the sum of pixel changes detected during the defined time interval (5 minutes). Larval behavior was depicted as mean actinteg units per 5 minutes in the 30 minute recording period and over consecutive time intervals. Data are expressed as mean±SD for single experiments with regards to screening, and as mean±SEM for single experiments and for independent experiments of which the means or data are pooled.

In the first secondary screen three replicate wells were used per sample (100 μg/mL) tested and each experimental plate contained 12 internal control wells. In the second secondary screen six replicate wells were used per sample and concentration tested (100, 33, and 11 μg/mL), again 12 internal control wells were used per experimental plate.

1.7. Electrophysiology

Non-invasive LFP recordings were measured from the midbrain (optic tectum) of 7 dpf zebrafish larvae pre-incubated with VHC only, PTZ only, compound and VHC, or compound and PTZ. Experiments were performed as described in Copmans et al. (2018) Neurochem. Int. 112, 124-133;

Copmans (2018) ACS chemical neuroscience. In brief, larvae were incubated for approximately 2 hours with VHC (1% DMSO) or test compound (1% DMSO) in a 100 μL volume. After incubation, an equal volume of VHC (embryo medium) or 40 mM PTZ (20 mM working concentration) was added to the well for 15 minutes prior to recording. These steps occurred at 28° C., while further manipulation and electrophysiological recordings occurred at room temperature (±21° C.). The larva was embedded in 2% low melting point agarose (Invitrogen) and the signal electrode (an electrode inside a soda-glass pipet (1412227, Hilgenberg) pulled with a DMZ Universal Puller (Zeitz, Germany), diameter±20 microns, containing artificial cerebrospinal fluid (ACSF: 124 mM NaCl, 10 mM glucose, 2 mM KCl, 2 mM $MgSO_4$, 2 mM $CaCl_2$, 1.25 mM $KH_2PO_4$, and 26 mM $NaHCO_3$, 300-310 mOsmols)) was positioned on the skin covering the optic tectum. A differential extracellular amplifier (DAGAN, USA) amplified the voltage difference between the signal (measured by the signal electrode) and the reference electrode. The differential signal was band pass filtered at 0.3-300 Hz and digitized at 2 kHz via a PCI-6251 interface (National instruments, UK) using WinEDR (John Dempster, University of Strathclyde, UK). A grounding electrode grounded the electrical system. All electrodes were connected with ACSF. Each recording lasted 600 seconds. Manual analysis was completed by quantification of the number, cumulative duration, and mean duration of epileptiform-like events with Clampfit 10.2 software (Molecular Devices Corporation, USA). An electrical discharge was considered epileptiform if it was a poly-spiking event comprising at least 3 spikes with a minimum amplitude of three times the baseline amplitude and a duration of at least 100 milliseconds. Data are expressed as mean±SD.

1.8 Mouse 6-Hz Psychomotor Seizure Model 1.8. Mouse 6-Hz Psychomotor Seizure Model Experiments were performed as described in Copmans et al. (2018) *ACS chemical neuroscience*. In brief, 50 μL (injection volume was adjusted to the individual weight) of VHC (PEG200:DMSO 1:1) or treatment (an ASD or test compound dissolved in VHC) was i.p. injected in NMRI mice (average weight 32 g, range 28-36 g) and after 30 minutes psychomotor seizures were induced by low frequency, long duration corneal electrical stimulation (6 Hz, 0.2 ms rectangular pulse width, 3 s duration, 44 mA) using an ECT Unit 5780 (Ugo Basile, Comerio, Italy). Mice were manually restrained and a drop of ocular anesthetic (0.5% lidocaine) was applied to the corneas before stimulation. Following electrical current stimulation, the mouse was released in a transparent cage for behavioral observation, which was video-recorded. VHC-treated mice typically displayed stun, twitching of the vibrissae, forelimb clonus, and Straub tail. In addition, facial and mouth jerking as well as head nodding were observed occasionally. Seizure durations were measured during the experiment by experienced researchers, familiar with the different seizure behaviors. In addition, seizure durations were determined by blinded video analysis to confirm or correct the initial observations. Data are expressed as mean±SD.

Example 2

Zebrafish-Based Antiseizure Drug Discovery 2009 marine NPs, i.e., extracts and pre-fractionated fractions, provided by the different PharmaSea partners, were screened for neuroactivity at a concentration of 100 μg/mL (2 hours incubation time) using the zebrafish PMR assay.

The PMR was described by a behavioral fingerprint of 16 pseudo Z-scores that represent the embryonic motion over a 30 second recording period using the first and third quantile (Q1 and Q3) for each of the 8 time periods. A neuroactive hit was defined as a marine NP that modified the PMR such that its behavioral fingerprint contained at least one pseudo Z-score with an absolute value equal to or exceeding 5. Each PMR-assay was followed by visual evaluation of the embryos under a light microscope to assess toxicity of treatment. Only 109 marine NPs were observed to cause toxicity. All other treatments did not induce toxicity under the test conditions, whereof 332 were neuroactive and 1568 samples were inactive. The 332 neuroactive hits underwent antiseizure analysis at a concentration of 100 µg/mL (2 hours incubation time) using the zebrafish PTZ seizure model. In this model the convulsant PTZ (20 mM) is administered to the swimming water of 7 days post-fertilization (dpf) larvae and induces typical seizure-like behavior that is characterized by high-speed swimming, whirlpool-like circling, clonus-like seizures, and loss of posture. An antiseizure hit was defined as a marine NP that significantly lowered the strongly elevated larval locomotion as a result of PTZ-induced seizures. Initially, 97 antiseizure hits were identified that did not result in toxicity, whereof 43 were confirmed in a second screen using twice the number of larvae per sample. Moreover, the latter screen investigated concentration-dependent effects by analyzing a three-fold serial dilution from 100 µg/mL onwards. Hit prioritization was based on efficacy, concentration-dependency, and sample availability.

Figure 3:
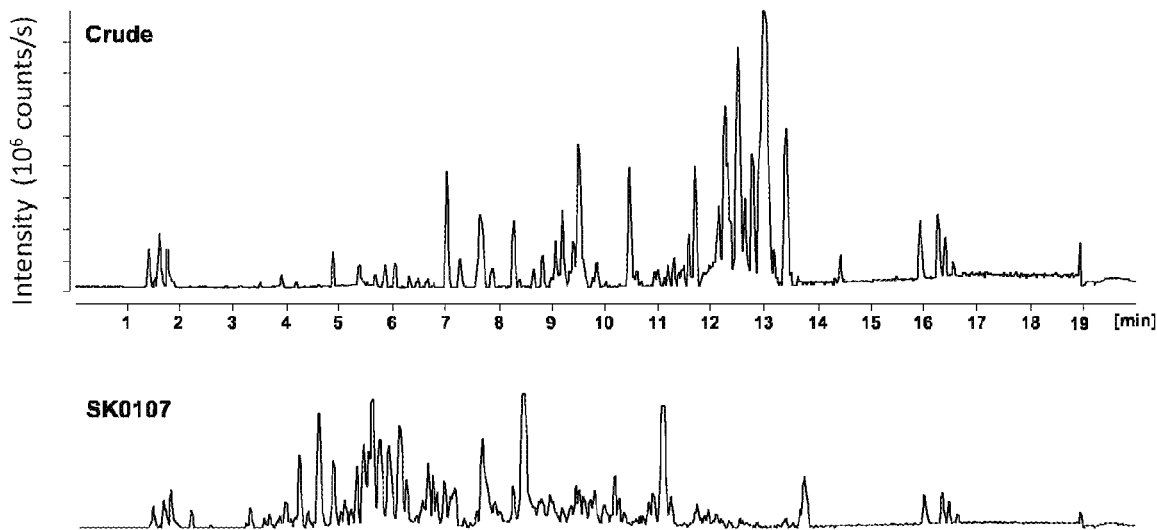
FIG. 3. Antiseizure hit SK0107. (A) *Aspergillus insuetus* IBT 28443 cultivated on Czapek Yeast extract agar (CYA) and Yeast extract sucrose agar (YES) media for 9 days at 25° C. in the dark. Base peak chromatograms of the crude extract and bioactive fraction SK0107 in positive electrospray ionization mode. (B, C) Antiseizure activity of SK0107 in the zebrafish pentylenetetrazole (PTZ) seizure model after 2 hours of incubation. PTZ-induced seizure-like behavior is expressed as mean actinteg units per 5 minutes (±SEM) during the 30 minutes recording period (B) and over consecutive time intervals (C). Means are pooled from three independent experiments with each 12 replicate wells per condition. Statistical analysis: (B) one-way ANOVA with Dunnett's multiple comparison test, (C) two-way ANOVA with Bonferroni posttests (GraphPad Prism 5). Significance levels: $*p \leq 0.05$; $p \leq 0.01$; $*p \leq 0.001$. Abbreviation: vehicle, VHC.
Figure 3:
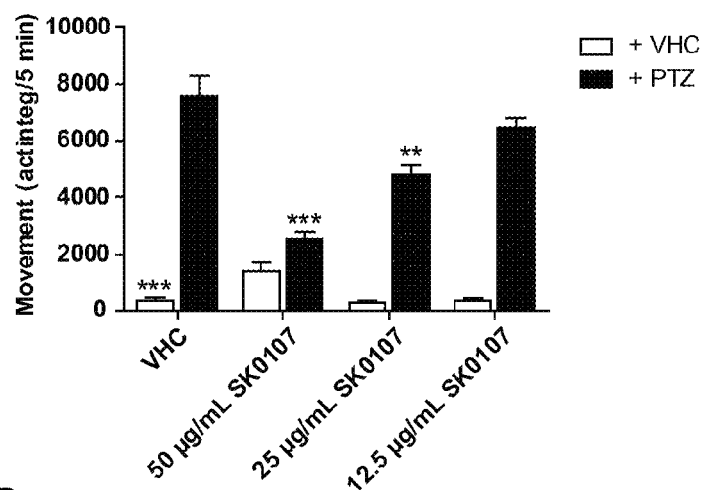
Figure 3:
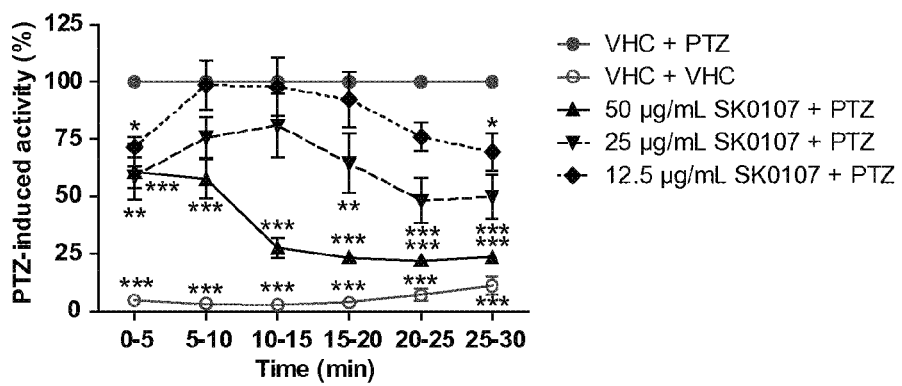

Among prioritized hits was marine NP SK0107, one of the more polar fractions from initial reverse phase chromatographic separation of the crude extract of *Aspergillus insuetus* IBT 28443 (FIG. 3A), which was isolated from a seawater trap set in the North Sea, in between Norway and Denmark. *Aspergillus insuetus* is a filamentous fungus belonging to *Aspergillus* section Usti that includes species from soil, foods, and indoor air environments but also from marine isolates. Marine-derived fungal isolates with *Aspergillus* species as a common source, have been seen to yield a plethora of biologically active compounds including structurally unique secondary metabolites. Prior to further experiments the maximum tolerated concentration (MTC) of SK0107 was determined, which was defined as the highest concentration at which no larvae died nor showed signs of toxicity or locomotor impairment in comparison to vehicle (VHC)-treated control larvae. The MTC was observed to be 50 µg/mL and used as the highest test concentration in all subsequent tests. To validate the results obtained during the course of screening the antiseizure activity of SK0107 was investigated in the larval zebrafish PTZ seizure model at the MTC, MTC/2, and MTC/4 (two-fold serial dilution, 2 hours incubation time) in three independent experiments (FIG. 3B-C). In line with former results, the antiseizure hit SK0107 showed significant concentration-dependent activity against PTZ-induced seizure behavior, both during the 30 minute (min) recording period ($p \leq 0.001$ and $p \leq 0.01$) (FIG. 3B) as within 5 min time intervals ($p \leq 0.001$, $p \leq 0.01$, and $p \leq 0.05$) (FIG. 3C).

Example 3

Bioactivity-Guided Identification of Active Compounds

To identify the active constituents of SK0107 that are responsible for its antiseizure activity bioactivity-guided purification was performed of *Aspergillus insuetus* IBT 28443. In the crude extract of *Aspergillus insuetus* dereplication using ultra-high performance liquid chromatography-diode array detection-quadrupole time of flight mass spectrometry (UHPLC-DAD-QTOFMS) tentatively identified an abundant presence of the sesterterpenoids, ophiobolins (inactive, data not shown). Before any large scale cultivation, small scale extracts were prepared of the fungus cultivated individually on CYA, YES and OAT media, as the tested bioactive extract was of the combined cultivation on both CYA and YES media. This was done in hope of finding a medium where the production of ophiobolins was reduced and other compounds presented in a higher concentration than the original crude extract. CYA medium was chosen based on the activity of fractions from the crude extract and based on the reduced concentration of ophiobolins (data not shown).

Figure 4:
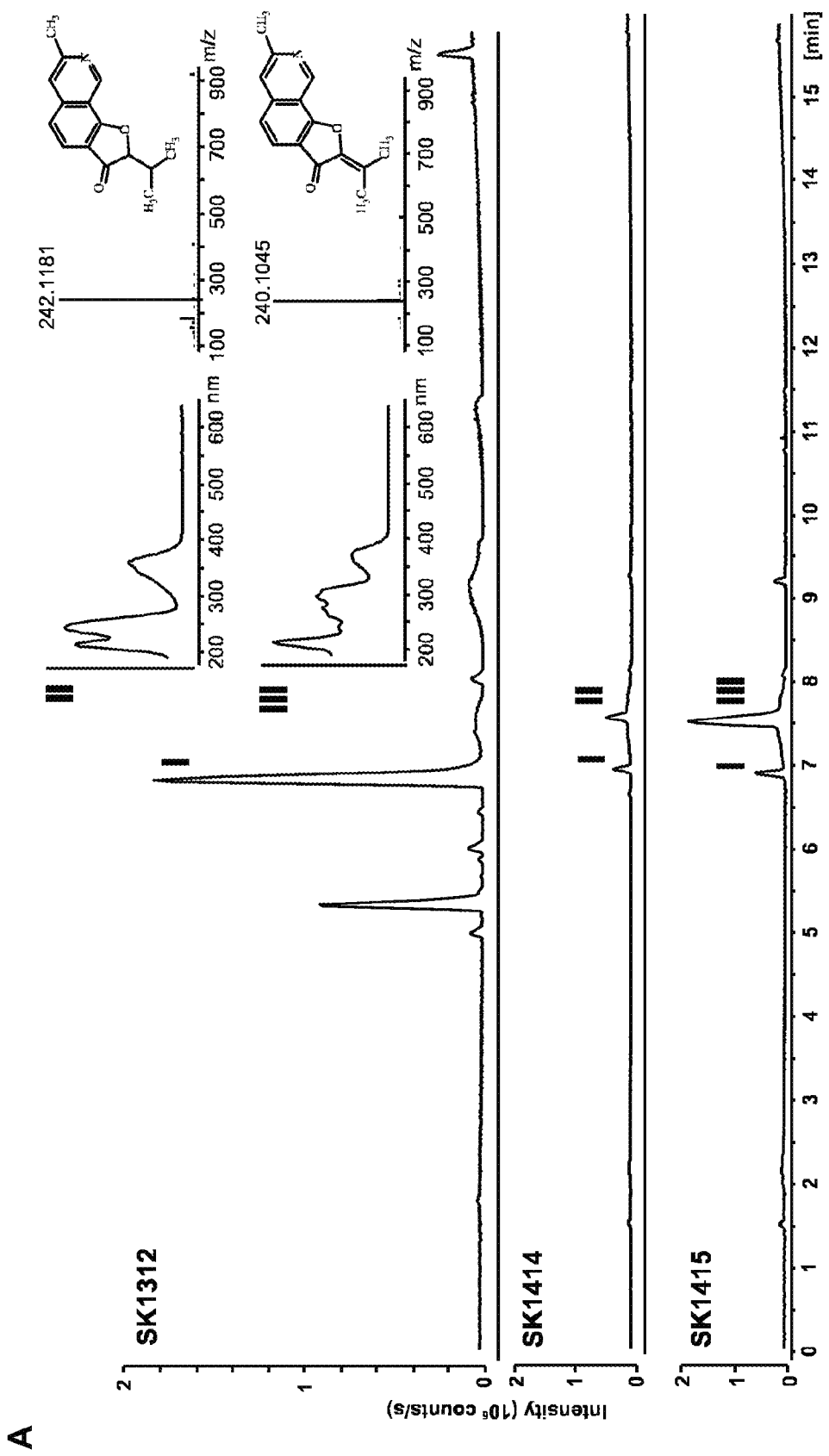
FIG. 4. Bioactivity-guided identification of the active compounds of antiseizure hit SK0107. (A) *Aspergillus insuetus* IBT 28443 cultivated on CYA media for 9 days in the dark at 25° C. Base peak chromatogram (BPC) of the most bioactive fraction (SK1312) from first reversed phase fractionation in positive electrospray ionization mode. BPC chromatograms of the two most bioactive fractions (SK1414 and SK1415) from the second reversed phase fractionation in positive electrospray ionization mode. UV and HRMS spectra for TMC-120A (II) and UV and HRMS spectra for TMC-120B (III). (B-D) Antiseizure activity of SK1312 (n=23-24 replicate wells per condition) (B), SK1414 (n=10-11 replicate wells per condition) (C), and SK1415 (n=22 replicate wells per condition) (D) in the zebrafish pentylenetetrazole (PTZ) seizure model after 2 hours of incubation at their maximum tolerated concentration (MTC), MTC/2, and MTC/4. PTZ-induced seizure-like behavior is expressed as mean actinteg units per 5 minutes (±SEM) during the 30 minutes recording period. (B, D) Data are pooled from two independent experiments with each 11-12 replicate wells per condition. (B-D) Statistical analysis: one-way ANOVA with Dunnett's multiple comparison test for comparison of sample+PTZ groups with vehicle (VHC)+PTZ control group, Kruskal-Wallis test with Dunn's multiple comparison test for comparison of sample+VHC groups with VHC+VHC control group (GraphPad Prism 5). Significance levels: $*p \leq 0.05$; $p \leq 0.01$; $*p \leq 0.001$.
Figure 4:
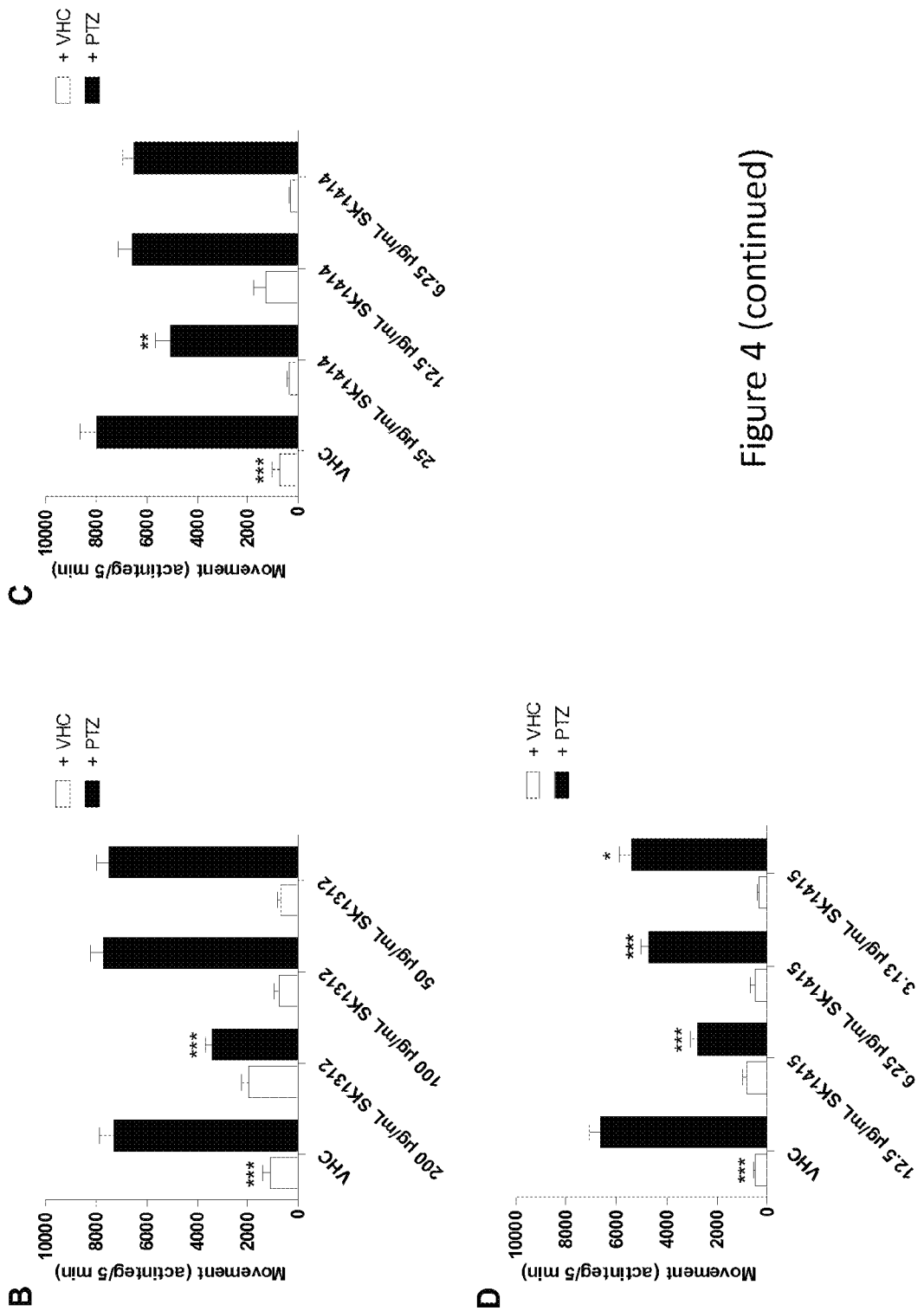

A large scale extract was prepared from cultivation of *Aspergillus insuetus* IBT 28443 on CYA media for 9 days in the dark at 25° C. and bioactivity-guided purification was performed through several reversed phase purification steps until single compound isolation. In the two most bioactive fractions from the second fractionation of the crude extract, i.e., SK1414 and SK1415 (FIG. 4C-D), three compounds were tentatively identified by UHPLC-DAD-QTOFMS (FIG. 4A). One compound with the pseudomolecular ion, $[M+H]^+$ m/z 351.1818 (mass accuracy −0.77 ppm) and two related compounds that were seen to coelute by first fractionation with the pseudomolecular ions, $[M+H]^+$ m/z 242.1177 (mass accuracy −0.32 ppm) and m/z 240.1019 (mass accuracy 0.14 ppm). The molecular formulas was based on the pseudomolecular ions m/z 242.1177 and m/z 240.1019 established to be $C_{15}H_{15}NO_2$ and $C_{15}H_{13}NO2$ respectively. A search in Antibase2012 for the formulas revealed the possible candidates to be the isoquinoline alkaloids TMC-120A and TMC-120B for the two related compounds (FIG. 4A). This was supported by UV/vis data consistent with litterature, with both compounds displaying characteristic UV/vis spectra, and production by related fungal species (*Aspergillus ustus*). The structure of TMC-120B was confirmed by elucidation with 1D and 2D NMR spectroscopy and comparison of $^1H$ and $^{13}C$ chemical shifts to literature data [Kohno et al (1999) *Tetrahedron* 55, 11247-11252]. As only trace amounts of compounds TMC-120A and TMC-120B could be purified from the crude extract of *Aspergillus insuetus* IBT 28443, various closely related species belonging to *Aspergillus* section Usti (Table 1) were investigated by HRMS, MS/HRMS and UV/vis data to find a better fungal producer. *Aspergillus insuetus* IBT 28485 was chosen based on its production of TMC-120A and TMC-120B as some of the main compounds. TMC-120A and TMC-120B were purified in higher amounts (10 mg), and the structure of TMC-120A was confirmed by 1D and 2D NMR spectroscopy and comparison of $^1H$ and $^{13}C$ chemical shifts and optical rotation to literature data [Kohno et al (1999) *Tetrahedron* 55, 11247-11252]. Some of the fungus other major metabolites were isolated i.e. the structural analogues TMC-120C, penicisochroman G and ustusorane B with HRMS, UV/Vis and $^1H$ and $^{13}C$ NMR data consistent with literature [Kohno et al (1999) *Tetrahedron* 55, 11247-11252, Bunbamrung et al (2014) *Phytochem. Lett.* 10, 13-18, Lu et al (2009) *J. Nat. Prod.* 72, 1761-1767].

TABLE 1

Potential TMC-120A and TMC-120B producing strains from *Aspergillus* section *Usti*.

| IBT number | Species |
|---|---|
| 4133 | *Aspergillus ustus* |
| 10619 | *Aspergillus ustus* |
| 28485 | *Aspergillus insuetus* |
| 914826 | *Aspergillus calidoustus* |

Closely related species belonging to *Aspergillus* section *Usti* from the IBT culture collection at the Department of Biotechnology and Biomedicine that are potential TMC-120A and TMC-120B producing strains.

Table 2 shows NMR spectroscopic data (400 MHz, CDCl$_3$, δ in ppm, J in Hz) for TMC-120B isolated from the crude extract of *Aspergillus insuetus* IBT 28443.

TABLE 2

NMR spectroscopic data for TMC-120B

| | TMC-120B | |
|---|---|---|
| Position | δ$_H$ (mult, J) | δ$_C$ |
| 1 | — | — |
| 2 | — | 145.6 |
| 3 | — | 182.1 |
| 3a | — | 119.3 |
| 4 | 7.81 d(8.6) | 124.4 |
| 5 | 7.36 d(8.6) | 120.8 |
| 5a | — | 141.3 |
| 6 | 7.53 s | 119.8 |
| 7 | — | 156.7 |
| 8 | — | — |
| 9 | 9.55 s | 146.3 |
| 9a | — | 114.6 |
| 9b | — | 164.0 |
| 10 | 2.74 s | 24.9 |
| 11 | — | 133.7 |
| 12 | 2.42 s | 17.6 |
| 13 | 2.24 s | 20.5 |

Table 3 shows NMR spectroscopic data (800 MHz, CDCl$_3$, δ in ppm, J in Hz) for TMC-120A and TMC-120B isolated from the crude extract of *Aspergillus insuetus* IBT 28485

TABLE 3

NMR spectroscopic data for TMC-120A and TMC-120B

| | TMC-120A | | TMC-120B | |
|---|---|---|---|---|
| Position | δ$_H$ (mult, J) | δ$_C$ | δ$_H$ (mult, J) | δ$_C$ |
| 1 | — | — | — | — |
| 2 | 4.85 d(4.0) | 91.8 | — | 145.8 |
| 3 | — | 199.8 | — | 182.4 |
| 3a | — | 117.8 | — | 119.6 |
| 4 | 7.71 d(8.6) | 124.3 | 7.80 d(8.6) | 124.4 |
| 5 | 7.30 d(8.6) | 120.3 | 7.36 d(8.6) | 120.8 |
| 5a | — | 142.5 | — | 141.5 |
| 6 | 7.53 s | 119.9 | 7.53 s | 119.8 |
| 7 | — | 157.4 | — | 156.8 |
| 8 | — | — | — | — |
| 9 | 9.55 s | 146.6 | 9.54 s | 146.4 |
| 9a | — | 115.2 | — | 114.8 |
| 9b | — | 174.1 | — | 164.2 |
| 10 | 2.75 s | 24.7 | 2.74 s | 24.9 |
| 11 | 2.46 m | 31.3 | — | 134.0 |
| 12 | 0.92 d(6.9) | 15.9 | 2.42 s | 17.8 |
| 13 | 1.23 d(6.9) | 19.0 | 2.24 s | 20.6 |

Table 4 shows NMR spectroscopic data for penicisochroman G and ustusorane B (600 MHz, CDCl$_3$, δ in ppm, J in Hz) and TMC-120C (800 MHz, CDCl$_3$, δ in ppm, J in Hz) isolated from the crude extract of *Aspergillus insuetus* IBT 28485.

TABLE 4

NMR spectroscopic data for penicisochroman G, ustusorane B and TMC-120C

| | Penicisochroman G | | Ustusorane B | | TMC-120C | |
|---|---|---|---|---|---|---|
| Position | δ$_H$ (mult, J) | δ$_C$ | δ$_H$ (mult, J) | δ$_C$ | δ$_H$ (mult, J) | δ$_C$ |
| 1 | — | — | — | — | — | — |
| 2 | 4.39 d(3.9) | 90.4 | — | 144.6 | — | 110.3 |
| 3 | — | 200.6 | — | 182.2 | — | 198.7 |
| 3a | — | 120.0 | — | 120.7 | — | 115.8 |
| 4 | 7.43 d(8.0) | 123.9 | 7.52 d(8.0) | 122.9 | 7.52 d(8.2) | 124.5 |
| 5 | 6.57 d(8.0) | 117.0 | 6.63 d(8.0) | 116.2 | 6.99 d(8.2) | 119.6 |
| 5a | — | 142.0 | — | 139.6 | — | 142.1 |
| 6 | 5.65 s | 101.7 | 5.67 s | 100.7 | 7.14 s | 119.6 |
| 7 | — | 160.0 | — | 158.5 | — | 156.7 |
| 8 | — | — | — | — | — | — |
| 9 | 5.22 s | 62.8 | 5.26 s | 61.5 | 9.46 s | 146.8 |
| 9a | — | 108.9 | — | 107.7 | — | 114.7 |
| 9b | — | 168.3 | — | 158.9 | — | 171.6 |
| 10 | 1.95 s | 20.1 | 1.95 s | 18.7 | 2.50 s | 23.9 |
| 11 | 2.31 m | 31.2 | — | 129.9 | 2.40 m | 34.1 |
| 12 | 0.84 d(6.9) | 15.8 | 2.33 s | 16.2 | 0.96 | 16.1 |
| 13 | 1.13 d(6.9) | 19.0 | 2.06 s | 19.0 | 1.21 d(6.6) | 15.7 |

Example 4

TMC-120A and TMC-120B Ameliorate Seizures in the Zebrafish PTZ Seizure Model

Figure 5:
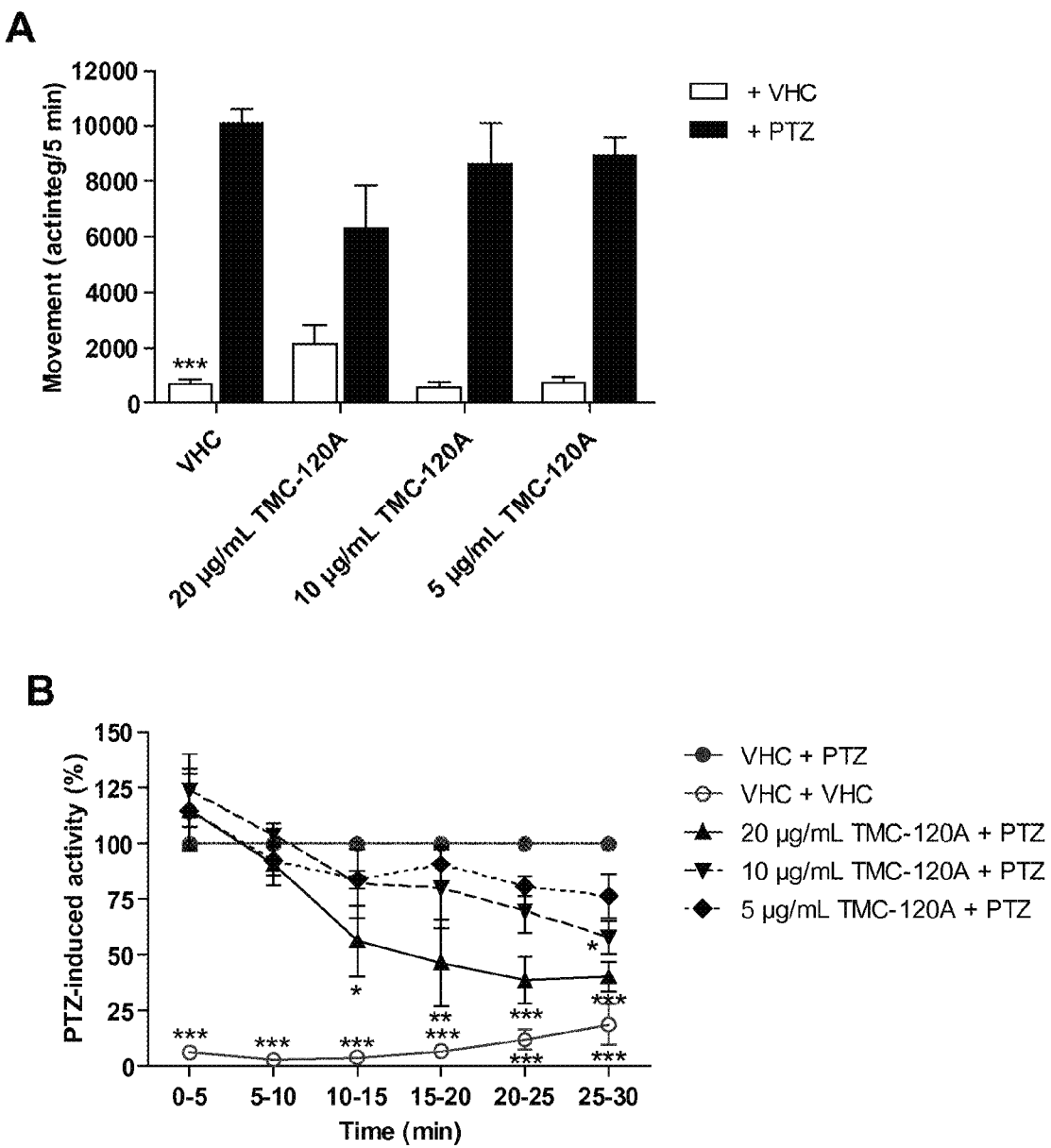
FIG. 5. Behavioral antiseizure analysis of TMC-120A and TMC-120B in the zebrafish PTZ seizure model. Antiseizure activity of TMC-120A (A, B), and TMC-120B (C, D) in the zebrafish pentylenetetrazole (PTZ) seizure model after 2 hours of incubation, respectively. PTZ-induced seizure-like behavior is expressed as mean actinteg units per 5 minutes (±SEM) during the 30 minutes recording period (A, C) and over consecutive time intervals (B, D). Means are pooled from three independent experiments with each 10-12 replicate wells per vehicle (VHC)+PTZ and compound+PTZ condition, and 6-12 replicate wells per VHC+VHC and compound+VHC condition. Statistical analysis: (A, C) one-way ANOVA with Dunnett's multiple comparison test, (B, D) two-way ANOVA with Bonferroni posttests (GraphPad Prism 5). Significance levels: *$p \leq 0.05$; $p \leq 0.01$; *$p \leq 0.001$.
Figure 5:
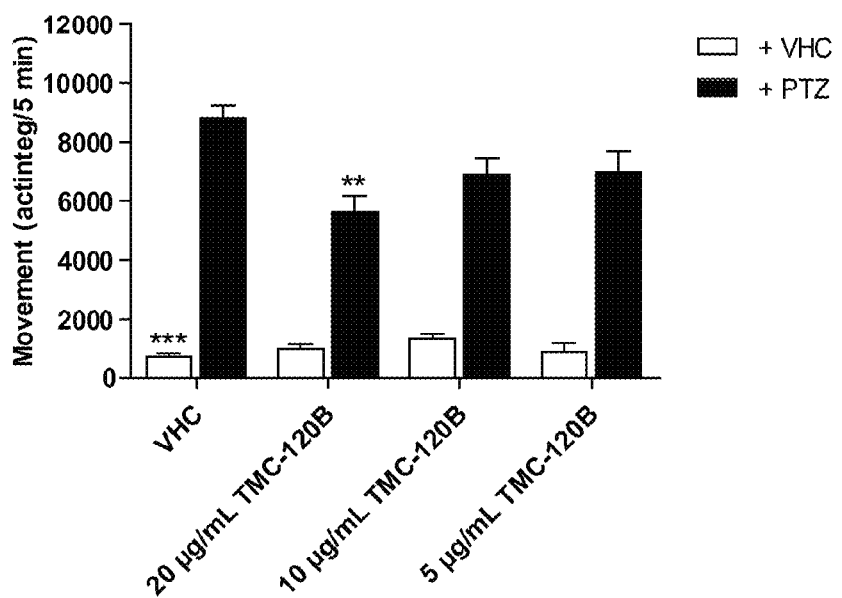
Figure 5:
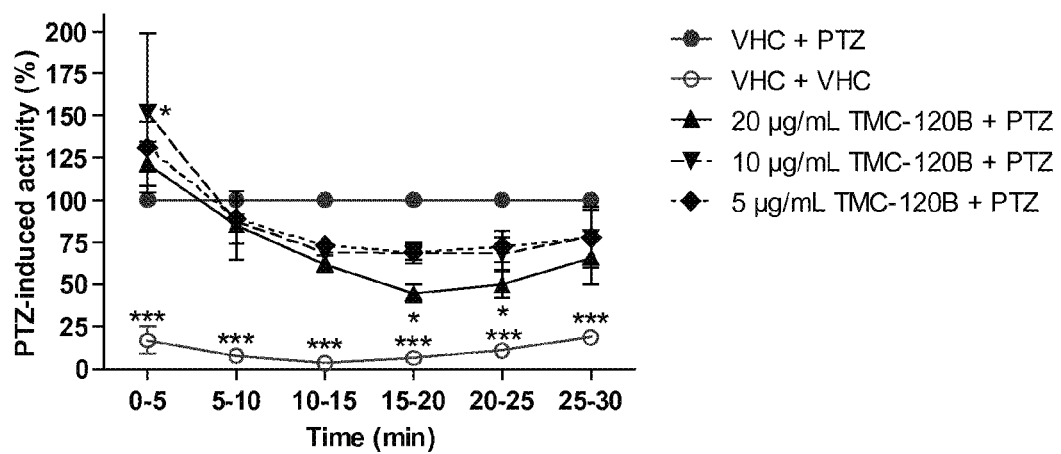

To confirm that TMC-120A and TMC-120B isolated from the most bioactive fractions are indeed the active constituents, their antiseizure activity was investigated in the zebrafish PTZ seizure model (FIG. 5). Larvae were treated with TMC-120A or TMC-120B for 2 hours, using their MTC, MTC/2, and MTC/4, conform with the conditions used for the crude extract and purified fractions. TMC-120B, but not TMC-120A, significantly lowered PTZ-induced seizure behavior at its MTC in the 30 min recording period (p≤0.01) (FIGS. 5A and C). A more detailed analysis of the 30 min recording period into 5 min time intervals revealed a significant reduction of PTZ-induced seizure behavior for both compounds at their MTCs. More specifically, within the 10-30 min time window with p≤0.05, p≤0.01, and p≤5.0.001 at different time intervals in case of TMC-120A and within the 15-25 min time window with p≤0.05 in case of TMC-120B (FIGS. 5B and D). No significant antiseizure activity was seen at lower concentrations, except for TMC-120A at the MTC/2 (p≤0.05) in the last 5 min time interval. These data demonstrate that TMC-120A and TMC-120B have antiseizure activity and confirm that the isolated compounds are indeed active constituents of the antiseizure hit SK0107, and the bioactive fractions SK1312, SK1414, and SK1415. The higher antiseizure efficacy of the bioactive extract and fractions in comparison to these observed for the individual compounds is possibly due to a synergistic action

Example 5

Figure 6:
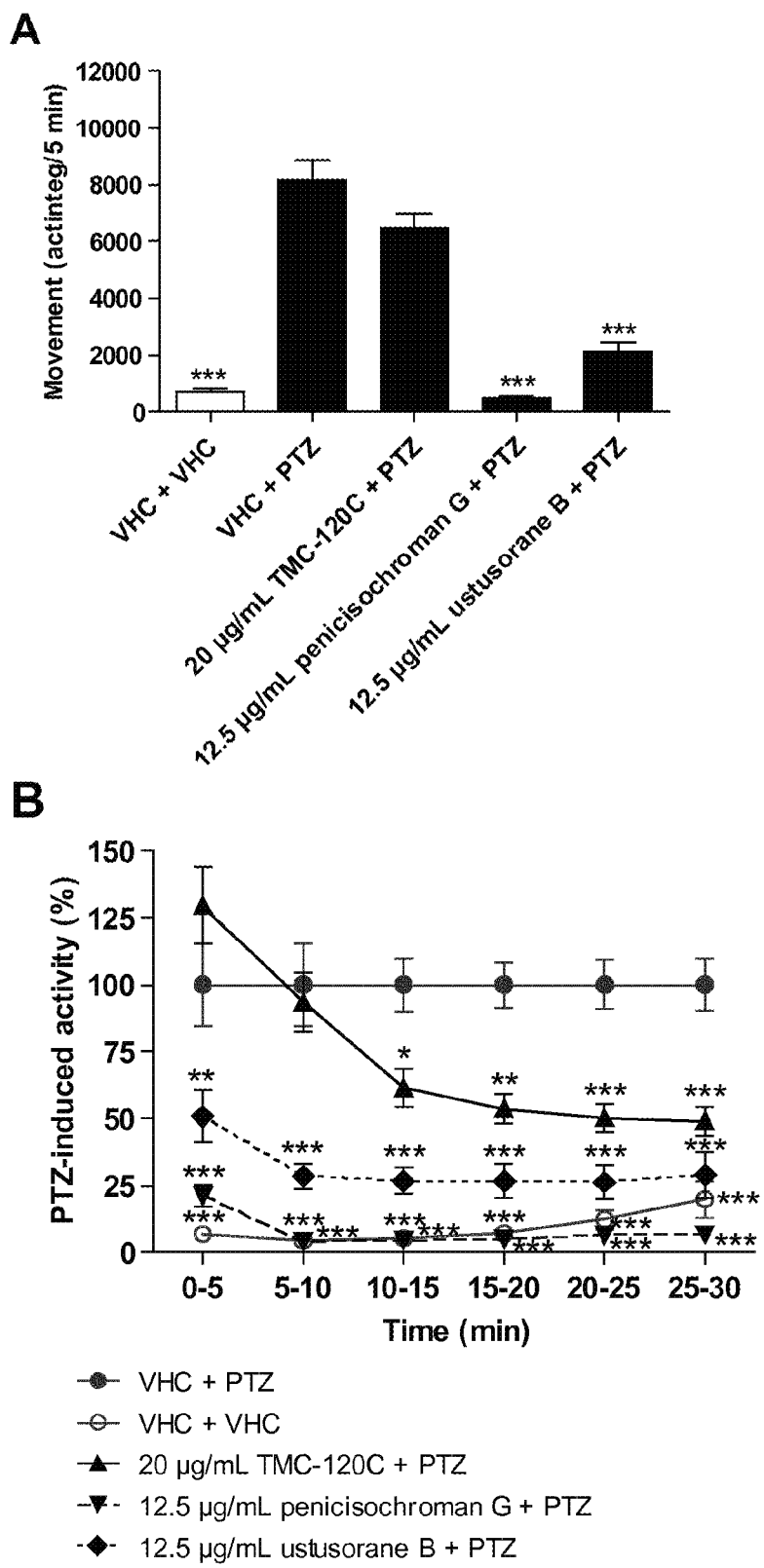
FIG. 6. Behavioral antiseizure analysis of TMC-120C, penicisochroman G and ustusorane B in the zebrafish PTZ seizure model. Antiseizure activity of TMC-120C, penicisochroman G, and ustusorane B in the zebrafish pentylenetetrazole (PTZ) seizure model after 2 hours of incubation. PTZ-induced seizure-like behavior is expressed as mean actinteg units per 5 minutes (±SEM) during the 30 minutes recording period (A) and over consecutive time intervals (B). Number of replicate wells per condition: 21-22 replicate wells for VHC+PTZ and VHC+VHC conditions, and 8-11 replicate wells for compound+PTZ condition. Statistical analysis: (A) one-way ANOVA with Dunnett's multiple comparison test, (B) two-way ANOVA with Bonferroni posttests (GraphPad Prism 5). Significance levels: *$p \leq 0.05$; $p \leq 0.01$; *$p \leq 0.001$.

TMC-120C, Penicisochroman G and Ustusorane B Ameliorate Seizures in the Zebrafish PTZ Seizure Model The antiseizure activity of TMC-120C, penicisochroman G and ustusorane B was investigated in the zebrafish pentylenetetrazole (PTZ) seizure model after 2 hours of incubation (FIG. 6). All three compounds lowered PTZ-induced seizure behavior in the 30 min recording period at the tested concentration, which was significant for penicisochroman G (p≤0.001) and ustusorane B (p≤0.001) (FIG. 6A). A more detailed analysis of the 30 min recording period into 5 min time intervals showed a significant reduction of PTZ-induced seizure behavior for all three compounds. More specifically, within the 10-30 min time window for TMC-120C (p≤0.05, p≤0.01 and p≤0.001) and over the entire recording period for penicisochroman G (0.001) and ustusorane B (p≤0.01 and p≤0.001) (FIG. 6B). Hence, TMC-120C, penicisochroman G and ustusorane B show antiseizure activity.

Example 6

Figure 7:
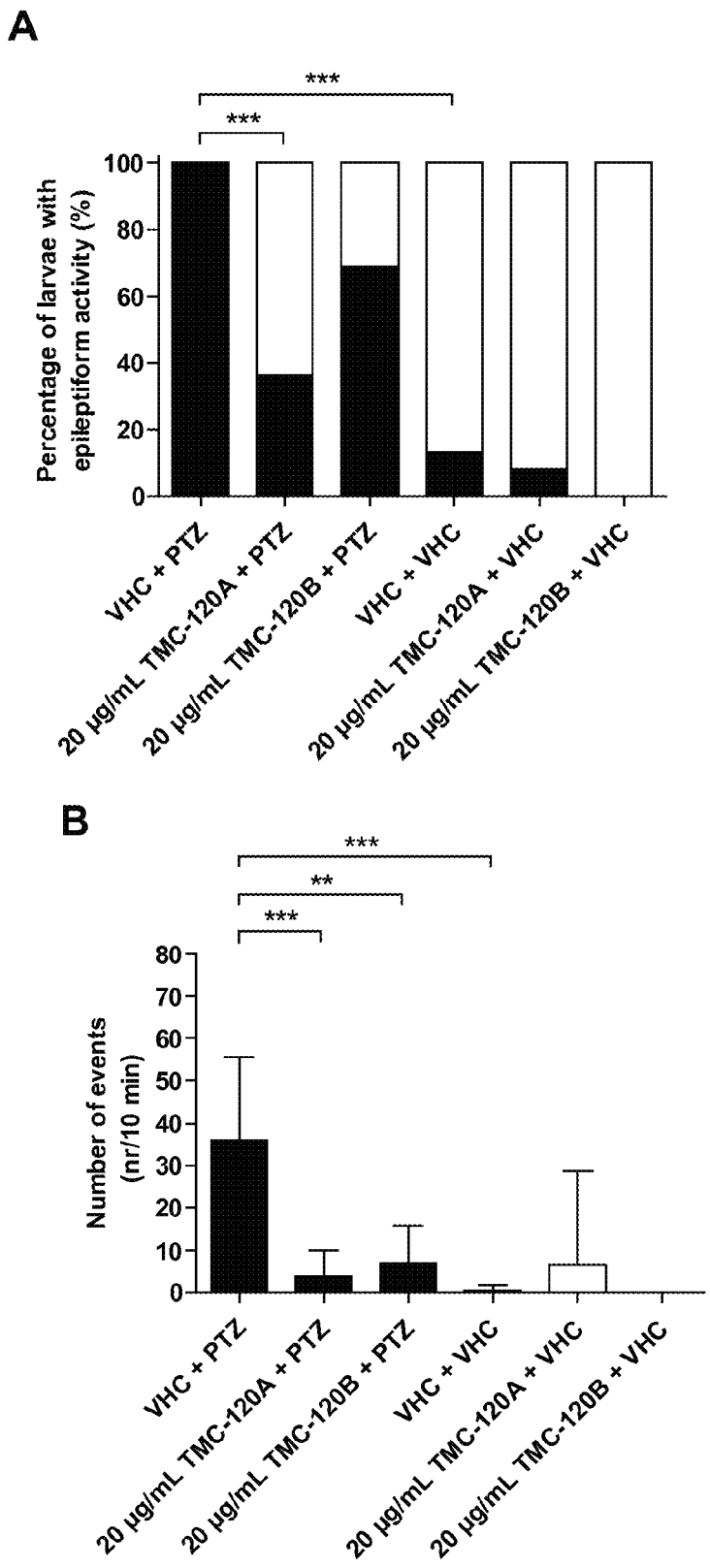
FIG. 7. Electrophysiological antiseizure analysis of TMC-120A and TMC-120B in the zebrafish PTZ seizure model. Noninvasive local field potential recordings from the optic tectum of larvae pre-exposed to vehicle (VHC) and pentylenetetrazole (PTZ), VHC only, compound and PTZ, or compound and VHC. Larvae were incubated with 20 μg/mL TMC-120A or TMC-120B for 2 hours, conform with the maximum tolerated concentrations and incubation time used in the behavioral assay. Epileptiform discharges are quantified by the number (mean±SD) (B) and cumulative duration (mean±SD) (C) of events per 10 minute recording. Larvae are considered to possess epileptiform brain activity when three or more events occurred during a 10 minute recording (A). Number of replicates per condition: 19 larvae were used for VHC+PTZ controls, 16 larvae were used for VHC+VHC controls, 13-14 larvae were used for compound+PTZ conditions, and 12 larvae were used for compound+VHC conditions. Statistical analysis: (A) Fisher's exact test with Bonferroni posttest, (B, C) Kruskal-Wallis test with Dunn's multiple comparison test (GraphPad Prism 5). Significance levels: *$p \leq 0.05$; $p \leq 0.01$; *$p \leq 0.001$.
Figure 7:
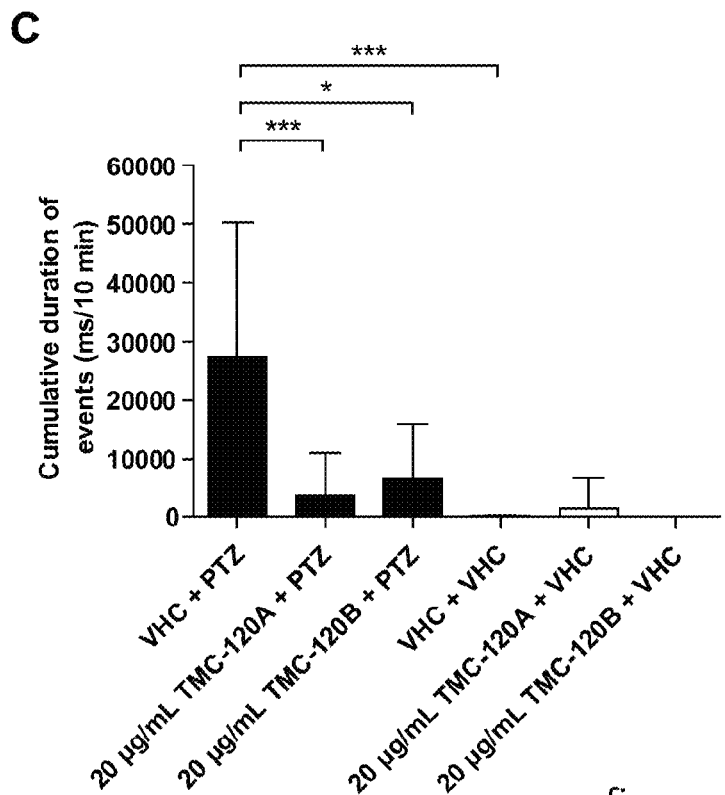

TMC-120A and TMC-120B Ameliorate Epileptiform Brain Activity in the Zebrafish PTZ Seizure Model To determine whether TMC-120A and TMC-120B besides antiseizure activity also ameliorate the PTZ-induced hyperexcitable state of the brain that is characterized by epileptiform discharges, local field potential (LFP) recordings were non-invasively measured from the midbrain (optic tectum) of zebrafish larvae (FIG. 7). Larvae were treated with either VHC or test compound (MTC and 2 hours incubation time were used in line with previous experiments) followed by a 15 min during exposure to PTZ or VHC prior to LFP measurements. Pre-exposure to PTZ but not to VHC resulted in a significant increase of epileptiform electrical discharges. Pre-incubation with TMC-120A significantly lowered the percentage of larvae with PTZ-induced epileptiform activity by more than half (0.001) (FIG. 7A). A larva was considered to have epileptiform brain activity when at least 3 electrical discharges were seen during the 10 min recording that fulfilled the pre-defined requirements of an epileptiform event (see methods). In addition, pre-incubation with TMC-120A or TMC-120B significantly lowered the number (p≤0.001, and p≤0.01, respectively) and the cumulative duration (p≤0.001, and p≤0.05, respectively) of PTZ-induced epileptiform events over the 10 min recording period (FIGS. 7B and C). Thus, TMC-120A and TMC-120B show anti-epileptiform activity and likely display their antiseizure properties by counteracting the hyperexcitable state of the brain.

Example 7

TMC-120A and TMC-120B Ameliorates Focal Seizures in the Mouse 6-Hz (44 mA) Psychomotor Seizure Model We investigated whether the antiseizure action of TMC-120A and TMC-120B observed in the larval zebrafish model translates to a standard rodent seizure model. From the available rodent seizure models we chose the mouse 6-Hz (44 mA) psychomotor seizure model, a gold standard in current ASD discovery efforts that is useful for screening and can detect compounds with novel antiseizure mechanisms and with potential against drug-resistant seizures. Seizures are characterized by a minimal clonic phase and stereotype automatistic behaviors, typically seen as stun, forelimb clonus, Straub tail, and twitching of the vibrissae [Barton et al. (2001) *Epilepsy Res* 47, 217-227; Buenafe et al. (2013) *ACS Chem Neurosci* 4, 1479-1487.]. Male NMRI mice were intraperitoneally (i.p.) injected with a 50 µL volume (adjusted to the individual weight) of VHC (DMSO: PEG200 1:1), positive control valproate (300 mg/kg), or TMC-120B (20, 10, 5, and 2.5 mg/kg) 30 min before electrical stimulation. VHC injected mice showed characteristic seizure behavior with a mean duration of 36 seconds and a minimum duration of 17 seconds. Hence, mice that had seizures for less than 17 seconds were considered to be protected. In line with previous studies, valproate treated mice were fully protected against the electrically-induced focal seizures as none of the mice showed any seizure after electrical stimulation. Mice i.p. injected with 10 mg/kg TMC-120B had a significantly shorter seizure duration than the VHC control group (p≤0.01) with a mean of 10 seconds. A dose-dependent reduction in antiseizure activity was seen for mice injected with 5 and 2.5 mg/kg TMC-120B (mean seizure duration of 23.5 and 27 seconds, respectively), as well as with the higher dose of 20 mg/kg (mean seizure duration of 27.5 seconds). The latter effect can be influenced by the poor solubility of 20 mg/kg TMC-120A in the solvent in contrast to the lower doses. Thus, the antiseizure activity of TMC-120B as observed in the larval zebrafish PTZ seizure model translates to a standard mouse model of drug-resistant focal seizures, thereby demonstrating the effectiveness of our zebrafish-based ASD discovery approach and the potential of marine NPs. Moreover, these observations confirm the translation from zebrafish larvae to mice in the field of epilepsy, as previously published [Patel and Patel (2011) *J. App. Pharm. Sci.* 1, 167-171; Perez et al. (2015) *J Biomol Screen* 20, 254-264].

Example 8

TMC-120A and TMC-120B Ameliorate Focal Seizures in the Mouse 6-Hz (44 mA) Psychomotor Seizure Model Despite the high genetic, physiological and pharmacological conservation, zebrafish are more distinct from humans than mammals [MacRae & Peterson (2015) *Nat Rev Drug Discov,* 14, 721-731; Wilcox et al. (2013) *Epilepsia* 54 S4, 24-34]. Therefore, we wanted to investigate whether the antiseizure action of TMC-120A and TMC-120B observed in the larval zebrafish model translates to a standard rodent seizure model. From the available rodent seizure models we chose the mouse 6-Hz (44 mA) psychomotor seizure model, a gold standard in current ASD discovery efforts that is useful for screening and can detect compounds with novel antiseizure mechanisms and with potential against drug-resistant seizures [Wilcox et al (2013) cited above; Barton (2001) *Epilepsy Res* 47(3), 217-227; Kehne et al. Neurochem Res (2017)]. It is an acute model of drug-resistant focal impaired awareness seizures [Fisher et al. (2017) *Epilepsia* 58 (4), 531-542], previously referred to as complex partial or psychomotor seizures [Holcomb & Dean in Psychomotor Seizures. In Encyclopedia of Child Behavior and Development, Goldstein, S.; Naglieri, J. A., Eds. Springer US: Boston, Mass., 2011; pp 1191-1192], that are induced by a low frequency, long duration corneal electrical stimulation [Kehne et al. (2017) Neurochem Res].

Figure 8:
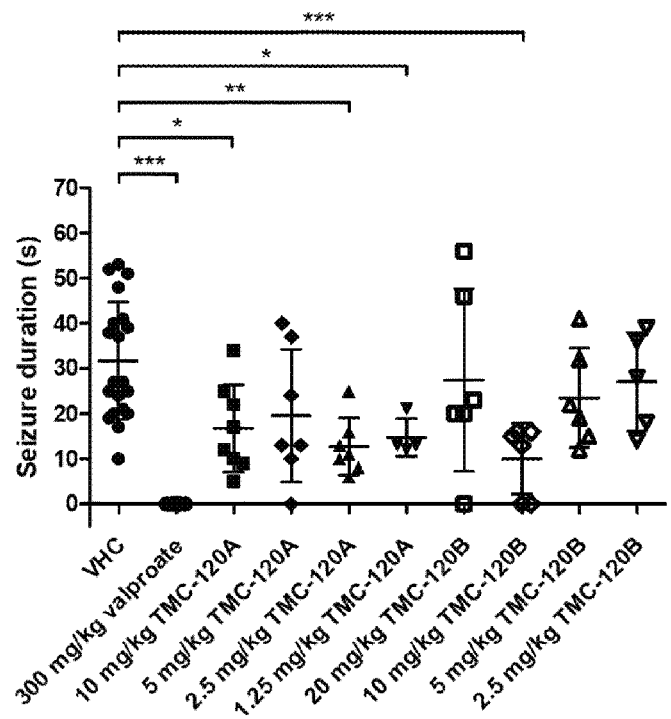
FIG. 8: Antiseizure activity analysis of TMC-120A and TMC-120B in the mouse 6-Hz psychomotor seizure model. Drug-resistant psychomotor seizures were induced by electrical stimulation (6 Hz, 0.2 ms rectangular pulse width, 3 s duration, 44 mA) through the cornea, 30 minutes after i.p. injection of vehicle (VHC, n=20), positive control valproate (n=12), TMC-120A (n=4-8), or TMC-120B (n=5-6). Mean seizure durations (±SD) are depicted. Statistical analysis: one-way ANOVA with Dunnett's multiple comparison test (GraphPad Prism 5). Significance levels: *$p \leq 0.05$; $p \leq 0.01$; *$p \leq 0.001$.

Male NMRI mice were intraperitoneally (i.p.) injected with a 50 µL volume (adjusted to the individual weight) of VHC (DMSO:PEG200 1:1), positive control valproate (300 mg/kg), TMC-120A (10, 5, 2.5, and 1.25 mg/kg), or TMC-120B (20, 10, 5, and 2.5 mg/kg) 30 min before electrical stimulation (FIG. 8). VHC injected mice showed characteristic seizure behavior with a mean (±SD) duration of 32 seconds (s) (±13 s). In line with previous studies, mice that were injected with valproate were fully protected against the induced seizures [Barton, M. (2001) cited above; Orellana-Paucar, et al. PLoS One 2013, 8 (12), e81634] as none of the mice showed any seizure after electrical stimulation ($p<0.001$). Mice i.p. injected with TMC-120A had a shorter seizure duration than the VHC control group, which was significant at 10 mg/kg ($p<0.05$, mean duration of 17 s (±10 s)), 2.5 mg/kg ($p<0.01$, mean duration of 13 s (±6 s)), and 1.25 mg/kg ($p<0.05$, mean duration of 15 s (±4 s)), but not at 5 mg/kg (mean duration of 20 s (±15 s)). Mice i.p. injected with TMC-120B also had a shorter seizure duration than the VHC control group, which was significant at 10 mg/kg ($p<0.001$, mean duration of 10 s (±8 s)). A non-significant dose-dependent reduction in seizure duration was seen for mice injected with 5 and 2.5 mg/kg TMC-120B (mean duration of 23.5 s (±11 s) and 27 s (±11 s), respectively). Finally, at the higher dose of 20 mg/kg also a non-significant reduction in seizure duration was seen with a mean seizure duration of 27.5 s (±20 s). The latter effect can be influenced by the poor solubility of 20 mg/kg TMC-120B in the solvent in contrast to the lower doses. Thus, the antiseizure activity of TMC-120A and TMC-120B that was observed in the larval zebrafish PTZ seizure model translates to a standard mouse model of drug-resistant focal seizures, thereby demonstrating the effectiveness of our zebrafish-based ASD discovery approach and the potential of marine NPs. Moreover, these observations confirm the translation of findings from zebrafish larvae to mice in the field of epilepsy, as previously published [Buenafe, et al. 2013) *ACS Chem Neurosci* 4(11), 1479-1487; Orellana-Paucar et al. (2012) *Epilepsy Behav* 24 (1), 14-22.

The invention claimed is:

1. A method for the treatment of epilepsy comprising administering to a subject in need thereof an isoquinoline or 1H-2-benzopyran selected from TMC-120A, TMC-120B, TMC-120C, penicisochroman G, ustusorane B, 7-methyl-furo[3,2-h]isoquinoline-3(2H)-one), and (2-(7-methyl-2,3-dihydrofuro[3,2-h]isoquinoline-2-yl)-propan-2-ol).

2. The method of claim 1, further comprising administering halimide and/or plinabulin to the subject.

3. The method of claim 2, further comprising administering halimide to the subject.

4. The method of claim 2, further comprising administering plinabulin to the subject.

* * * * *